US010066270B2

(12) United States Patent
Bussey et al.

(10) Patent No.: US 10,066,270 B2
(45) Date of Patent: Sep. 4, 2018

(54) METHODS AND KITS USED IN CLASSIFYING ADRENOCORTICAL CARCINOMA

(71) Applicant: THE TRANSLATIONAL GENOMICS RESEARCH INSTITUTE, Phoenix, AZ (US)

(72) Inventors: Kimberly J. Bussey, Phoenix, AZ (US); Michael J. Demeure, Scottsdale, AZ (US)

(73) Assignee: The Translational Genomics Research Institute, Phoenix, AZ (US)

( * ) Notice: Subject to any disclaimer, the term of this patent is extended or adjusted under 35 U.S.C. 154(b) by 0 days.

(21) Appl. No.: 15/490,871

(22) Filed: Apr. 18, 2017

(65) Prior Publication Data

US 2017/0226592 A1 Aug. 10, 2017

Related U.S. Application Data

(63) Continuation of application No. 14/807,561, filed on Jul. 23, 2015, now abandoned, which is a continuation of application No. 13/021,644, filed on Feb. 4, 2011, now abandoned.

(60) Provisional application No. 61/301,826, filed on Feb. 5, 2010.

(51) Int. Cl.
*C12Q 1/68* (2018.01)
*C12Q 1/6886* (2018.01)
*G01N 33/574* (2006.01)

(52) U.S. Cl.
CPC ..... *C12Q 1/6886* (2013.01); *G01N 33/57407* (2013.01); *C12Q 2600/112* (2013.01); *C12Q 2600/118* (2013.01); *C12Q 2600/158* (2013.01)

(58) Field of Classification Search
None
See application file for complete search history.

(56) References Cited

FOREIGN PATENT DOCUMENTS

| FR | 2918996 A1 | 1/2009 |
|---|---|---|
| WO | 2006119363 A2 | 11/2006 |
| WO | 2006119593 A1 | 11/2006 |
| WO | 2008132176 A2 | 11/2008 |
| WO | 2009126271 A1 | 10/2009 |

OTHER PUBLICATIONS

Giordano et al. (Clin Cancer Research Jan. 15, 2009 VOl 15 p. 668) (Year: 2009).*
Barlaskar, F.M. et al. 2009. Preclinical targeting of the type I insulin-like growth factor receptor in adrenocortical carcinoma. J Clin Endocrinol Metab 94(1):204-12.
Blake, J.A. et al. 2009. The Mouse Genome Database genotypes::phenotypes. Nucleic Acids Res 37(Database issue):D712-9.
Carter, S.L. et al. 2006. A signature of chromosomal instability inferred from gene expression profiles predicts clinical outcome in multiple human cancers. Nat Genet 38(9):1043-8.
Cohn, K. et al. 1986. Adrenocortical carcinoma. Surgery 100(6):1170-7. Abstract only.
De Fraipont, F. et al. 2005. Gene expression profiling of human adrenocortical tumors using complementary deoxyribonucleic Acid microarrays identifies several candidate genes as markers of malignancy. J Clin Endocrinol Metab 90(3):1819-29.
De Reynies, A. et al. 2009. Gene expression profiling reveals a new classification of adrenocortical tumors and identifies molecular predictors of malignancy and survival. J Clin Oncol 27(7):1108-15.
Decker, R.A. et al. 1991. Eastern Cooperative Oncology Group study 1879: mitotane and adriamycin in patients with advanced adrenocortical carcinoma. Surgery 110(6):1006-13.
Giordano, T.J. et al. 2003. Distinct transcriptional profiles of adrenocortical tumors uncovered by DNA microarray analysis. Am J Pathol 162(2):521-31.
Ignaszak-Szczepaniak, M. et al. 2006. The TP53 codon 72 polymorphism and predisposition to adrenocortical cancer in Polish patients. Oncol Rep 16(1):65-71.
Laurell, C. et al. 2009. Transcriptional profiling enables molecular classification of adrenocortical tumours. Eur J Endocrinol 161(1):141-52.
Lee, J.E. et al. 1995. Surgical management, DNA content, and patient survival in adrenal cortical carcinoma. Surgery 118(6)1090-8.
Paulson, T.G. et al. 1999. Loss of heterozygosity analysis using whole genome amplification, cell sorting, and fluorescence-based PCR. Genome Res 9(5):482-91.
Pfaffl, M.W. 2001. A new mathematical model for relative quantification in real-time RT-PCR. Nucleic Acids Res 29(9):e45.
Slater, E.P. et al. 2006. Analysis by cDNA microarrays of gene expression patterns of human adrenocortical tumors. Eur J Endocrinol 154(4):587-98.
Velazquez-Fernandez, D. et al. 2005. Expression profiling of adrenocortical neoplasms suggests a molecular signature of malignancy. Surgery 138(6):1087-94.
Weiss L.M. 1984. Comparative histologic study of 43 metastasizing and nonmetastasizing adrenocortical tumors. Am J Surg Pathol 8(3):163-9.
West, A.N. et al. 2007. Gene expression profiling of childhood adrenocortical tumors. Cancer Res 67(2):600-8.
Gentleman, R.C. et al. Genome Biol 5, R80 (2004).
Fenske, W. et al. 2009. Glucose transporter GLUT1 expression is an stage-independent predictor of clinical outcome in adrenocortical carcinoma. Endocrine Related Cancer 16(3):919-928.
Espina, A.G. et al. 2009. Induction of D1k1 by PTTG1 inhibits adipocyte differentiation and correlates with malignant transformation. Molecular Biology of the Cell 20(14):3353-3362.
Su M.C. et al. 2006. Overexpression of pituitary tumor-transforming gene-1 in hepatocellular carcinoma. Hepato-Gastroenterology 53(68):262-265.

(Continued)

*Primary Examiner* — Katherine D Salmon
(74) *Attorney, Agent, or Firm* — Rodney J. Fuller; Booth Udall Fuller, PLC

(57) ABSTRACT

The invention encompasses methods and kits used to detect biomarkers that may be used to predict disease outcome in adrenocortical carcinoma patients.

20 Claims, 6 Drawing Sheets
Specification includes a Sequence Listing.

(56) References Cited

OTHER PUBLICATIONS

Kakar, S.S. 1999. Molecular cloning, genomic organization and identification of the promoter for the human pituitary tumor transformation gene (PTTG). Gene 240:317-324.

Genkai, N. et al. 2006. Increased expression of pituitary tumor-transforming gene (PTTG)-1 is correlated with poor prognosis in glioma patients. Oncology Reports 15:1569-1574.

Shibata, Y. et al. 2002. Expression of PTTG (pituitary tumor transforming gene) in esophageal cancer. Jpn. J. Clin. Oncol. 32(7):233-237.

Fujii, T. et al. 2006. Overexpression of pituitary tumor transforming gene 1 in HCC is associated with angiogenesis and poor prognosis.

Ozimek A. et al., "Bilateral Primary Adrenal Non-Hodgkin's Lymphoma and Primary Adrenocortical Carcinoma Review of the Literature Preoperative Differentiation of Adrenal Tumors" Endocrine Journal 2008 vol. 55(4)625-638.

Van Ditzhuijsen C. et al., "Adrenocortical Carcinoma" The Netherlands Journal of Medicine 2007 vol. 65 (2) 55-59.

Vaughan E. et al., "Surgery of the Adrenals" The Scientific World Journal2004 vol. 4(81) 400-426.

Allolio B. et al., "Clinical Review: Adrenocortical Carcinoma: Clinical Update" The Journal of Clinical Endocrinology & Metabolism 2006 vol. 91(6) 2027-2037.

Communication from the European Patent Office for application serial No. 11740455.8 dated May 19, 2014.

European Search Report for application serial No. 11740455.8 dated Jun. 11, 2013.

International Search Report and Written Opinion of Searching Authority for PCT application No. PCT/US2011/023799 dated Oct. 6, 2011.

International Preliminary Report on Patentability for PCT application No. PCT/US2011/023799 dated Aug. 7, 2012.

\* cited by examiner

SEQUENCE LISTING

<160> NUMBER OF SEQ ID NOS: 23

<210> SEQ ID NO 1
<211> LENGTH: 671
<212> TYPE: DNA
<213> ORGANISM: Homo sapiens

<400> SEQUENCE: 1

```
gcggctgtta agacctgcaa taatccagaa tggctactct gatctatgtt gataaggaaa      60
atggagaacc aggcacccgt gtggttgcta aggatgggct gaagctgggg tctggacctt     120
caatcaaagc cttagatggg agatctcaag tttcaacacc acgttttggc aaaacgttcg     180
atgccccacc agccttacct aaagctacta gaaaggcttt gggaactgtc aacagagcta     240
```

-continued

| | |
|---|---|
| cagaaaagtc tgtaaagacc aagggacccc tcaaacaaaa acagccaagc tttctgcca | 300 |
| aaaagatgac tgagaagact gttaaagcaa aaagctctgt tcctgcctca gatgatgcct | 360 |
| atccagaaat agaaaaattc tttccttca atcctctaga ctttgagagt tttgacctgc | 420 |
| ctgaagagca ccagattgcg cacctcccct tgagtggagt gcctctcatg atccttgacg | 480 |
| aggagagaga gcttgaaaag ctgtttcagc tgggccccc ttcacctgtg aagatgccct | 540 |
| ctccaccatg ggaatccaat ctgttgcagt ctccttcaag cattctgtcg acctggatg | 600 |
| ttgaattgcc acctgtttgc tgtgacatag atatttaaat ttcttagtgc ttcagagttt | 660 |
| gtgtgtatttt g | 671 |

<210> SEQ ID NO 2
<211> LENGTH: 202
<212> TYPE: PRT
<213> ORGANISM: Homo sapiens

<400> SEQUENCE: 2

```
Met Ala Thr Leu Ile Tyr Val Asp Lys Glu Asn Gly Glu Pro Gly Thr
1               5                   10                  15

Arg Val Val Ala Lys Asp Gly Leu Lys Leu Gly Ser Gly Pro Ser Ile
            20                  25                  30

Lys Ala Leu Asp Gly Arg Ser Gln Val Ser Thr Pro Arg Phe Gly Lys
        35                  40                  45

Thr Phe Asp Ala Pro Pro Ala Leu Pro Lys Ala Thr Arg Lys Ala Leu
    50                  55                  60

Gly Thr Val Asn Arg Ala Thr Glu Lys Ser Val Lys Thr Lys Gly Pro
65                  70                  75                  80

Leu Lys Gln Lys Gln Pro Ser Phe Ser Ala Lys Lys Met Thr Glu Lys
                85                  90                  95

Thr Val Lys Ala Lys Ser Ser Val Pro Ala Ser Asp Asp Ala Tyr Pro
            100                 105                 110

Glu Ile Glu Lys Phe Phe Pro Phe Asn Pro Leu Asp Phe Glu Ser Phe
        115                 120                 125

Asp Leu Pro Glu Glu His Gln Ile Ala His Leu Pro Leu Ser Gly Val
    130                 135                 140

Pro Leu Met Ile Leu Asp Glu Glu Arg Glu Leu Glu Lys Leu Phe Gln
145                 150                 155                 160

Leu Gly Pro Pro Ser Pro Val Lys Met Pro Ser Pro Trp Glu Ser
                165                 170                 175

Asn Leu Leu Gln Ser Pro Ser Ser Ile Leu Ser Thr Leu Asp Val Glu
            180                 185                 190

Leu Pro Pro Val Cys Cys Asp Ile Asp Ile
        195                 200
```

<210> SEQ ID NO 3
<211> LENGTH: 5698
<212> TYPE: DNA
<213> ORGANISM: Homo sapiens

<400> SEQUENCE: 3

| | |
|---|---|
| aggttcaagt ggagctctcc taaccgacgc gcgtctgtgg agaagcggct tggtcggggg | 60 |
| tggtctcgtg gggtcctgcc tgtttagtcg ctttcagggt tcttgagccc cttcacgacc | 120 |
| gtcaccatgg aagtgtcacc attgcagcct gtaaatgaaa atatgcaagt caacaaaata | 180 |
| aagaaaaatg aagatgctaa gaaaagactg tctgttgaaa gaatctatca aagaaaaca | 240 |

```
caattggaac atattttgct ccgcccagac acctacattg gttctgtgga attagtgacc    300
cagcaaatgt gggtttacga tgaagatgtt ggcattaact atagggaagt cacttttgtt    360
cctggtttgt acaaaatctt tgatgagatt ctagttaatg ctgcggacaa caaacaaagg    420
gacccaaaaa tgtcttgtat tagagtcaca attgatccgg aaaacaattt aattagtata    480
tggaataatg aaaaggtat tcctgttgtt gaacacaaag ttgaaaagat gtatgtccca     540
gctctcatat ttggacagct cctaacttct agtaactatg atgatgatga aaagaaagtg    600
acaggtggtc gaaatggcta tggagccaaa ttgtgtaaca tattcagtac caaatttact    660
gtggaaacag ccagtagaga atacaagaaa atgttcaaac agacatggat ggataatatg    720
ggaagagctg gtgagatgga actcaagccc ttcaatggag aagattatac atgtatcacc    780
tttcagcctg atttgtctaa gtttaaaatg caaagcctgg acaaagatat tgttgcacta    840
atggtcagaa gagcatatga tattgctgga tccaccaaag atgtcaaagt ctttcttaat    900
ggaaataaac tgccagtaaa aggatttcgt agttatgtgg acatgtattt gaaggacaag    960
ttggatgaaa ctggtaactc cttgaaagta atacatgaac aagtaaacca caggtgggaa   1020
gtgtgtttaa ctatgagtga aaaaggcttt cagcaaatta gctttgtcaa cagcattgct   1080
acatccaagg gtggcagaca tgttgattat gtagctgatc agattgtgac taaacttgtt   1140
gatgttgtga agaagaagaa caagggtggt gttgcagtaa aagcacatca ggtgaaaaat   1200
cacatgtgga tttttgtaaa tgccttaatt gaaaacccaa cctttgactc tcagacaaaa   1260 gaaacatga ctttacaacc caagagcttt ggatcaacat gccaattgag tgaaaaattt    1320
atcaaagctg ccattggctg tggtattgta gaaagcatac taaactgggt gaagtttaag   1380
gcccaagtcc agttaaacaa gaagtgttca gctgtaaaac ataatagaat caagggaatt   1440
cccaaactcg atgatgccaa tgatgcaggg ggccgaaact ccactgagtg tacgcttatc   1500
ctgactgagg gagattcagc caaaactttg gctgtttcag gccttggtgt ggttgggaga   1560
gacaaatatg gggttttccc tcttagagga aaaatactca atgttcgaga gcttctcat   1620 aagcagatca tggaaaatgc tgagattaac aatatcatca agattgtggg tcttcagtac   1680
aagaaaaact atgaagatga agattcattg aagacgcttc gttatgggaa gataatgatt   1740
atgacagatc aggaccaaga tggttcccac atcaaaggct tgctgattaa ttttatccat   1800
cacaactggc cctctcttct gcgacatcgt tttctggagg aatttatcac tcccattgta   1860
aaggtatcta aaaacaagca agaaatggca ttttacagcc ttcctgaatt tgaagagtgg   1920
aagagttcta ctccaaatca taaaaaatgg aaagtcaaat attacaaagg tttgggcacc   1980
agcacatcaa aggaagctaa agaatacttt gcagatatga aagacatcg tatccagttc   2040 aaatattctg gtcctgaaga tgatgctgct atcagcctgg cctttagcaa aaaacagata   2100
gatgatcgaa aggaatggtt aactaatttc atggaggata aagacaacg aaagttactt   2160 gggcttcctg aggattactt gtatggacaa actaccacat atctgacata taatgacttc   2220
atcaacaagg aacttatctt gttctcaaat tctgataacg agagatctat cccttctatg   2280
gtggatggtt tgaaaccagg tcagagaaag gttttgttta cttgcttcaa acggaatgac   2340
aagcgagaag taaggttgc ccaattagct ggatcagtgg ctgaaatgtc ttcttatcat    2400
catggtgaga tgtcactaat gatgaccatt atcaatttgg ctcagaattt tgtgggtagc   2460
aataatctaa acctcttgca gcccattggt cagtttggta ccaggctaca tggtggcaag   2520
gattctgcta gtccacgata catctttaca atgctcagct ctttggctcg attgttattt   2580
ccaccaaaag atgatcacac gttgaagttt ttatatgatg acaaccagcg tgttgagcct   2640
```

```
gaatggtaca ttcctattat tcccatggtg ctgataaatg gtgctgaagg aatcggtact    2700
gggtggtcct gcaaaatccc caactttgat gtgcgtgaaa ttgtaaataa catcaggcgt    2760
ttgatggatg gagaagaacc tttgccaatg cttccaagtt acaagaactt caagggtact    2820
attgaagaac tggctccaaa tcaatatgtg attagtggtg aagtagctat tcttaattct    2880
acaaccattg aaatctcaga gcttcccgtc agaacatgga cccagacata caagaacaa     2940
gttctagaac ccatgttgaa tggcaccgag aagacacctc ctctcataac agactatagg    3000
gaataccata cagataccac tgtgaaattt gttgtgaaga tgactgaaga aaaactggca    3060
gaggcagaga gagttggact acacaaagtc ttcaaactcc aaactagtct cacatgcaac    3120
tctatggtgc ttttttgacca cgtaggctgt ttaaagaaat atgacacggt gttggatatt    3180
ctaagagact tttttgaact cagacttaaa tattatggat taagaaaaga atggctccta    3240
ggaatgcttg gtgctgaatc tgctaaactg aataatcagg ctcgctttat cttagagaaa    3300
atagatggca aaataatcat tgaaaataag cctaagaaag aattaattaa agttctgatt    3360
cagaggggat atgattcgga tcctgtgaag gcctggaaag aagcccagca aaaggttcca    3420
gatgaagaag aaaatgaaga gagtgacaac gaaaaggaaa ctgaaaagag tgactccgta    3480
acagattctg gaccaacctt caactatctt cttgatatgc ccctttggta tttaaccaag    3540
gaaaagaaag atgaactctg caggctaaga aatgaaaaag aacaagagct ggacacatta    3600
aaaagaaaga gtccatcaga tttgtggaaa gaagacttgg ctacatttat tgaagaattg    3660
gaggctgttg aagccaagga aaacaagat gaacaagtcg acttcctgg gaagggggg      3720
aaggccaagg ggaaaaaaac acaaatggct gaagttttgc cttctccgcg tggtcaaaga    3780
gtcattccac gaataaccat agaaatgaaa gcagaggcag aaaagaaaaa taaaagaaa     3840
attaagaatg aaaatactga aggaagccct caagaagatg gtgtggaact agaaggccta    3900
aaacaaagat tagaaaagaa acagaaaaga gaaccaggta caaagacaaa gaaacaaact    3960
acattggcat ttaagccaat caaaaaagga aagaagagaa atccctggtc tgattcagaa    4020
tcagatagga gcagtgacga aagtaatttt tgatgtccctc cacgagaaac agagccacgg    4080
agagcagcaa caaaaacaaa attcacaatg gatttggatt cagatgaaga tttctcagat    4140
tttgatgaaa aaactgatga tgaagatttt gtcccatcag atgctagtcc acctaagacc    4200
aaaacttccc caaacttag taacaaagaa ctgaaccac agaaagtgt cgtgtcagac      4260
cttgaagctg atgatgttaa gggcagtgta ccactgtctt caagccctcc tgctacacat    4320
ttcccagatg aaactgaaat tacaaacccca gttcctaaaa agaatgtgac agtgaagaag    4380
acagcagcaa aaagtcagtc ttccaccccc actaccggtg ccaaaaaaag ggctgcccca    4440
aaggaacta aaggggatcc agctttgaat tctggtgtct ctcaaaagcc tgatcctgcc     4500
aaaaccaaga atcgccgcaa aaggaagcca tccacttctg atgattctga ctctaatttt    4560
gagaaaattg tttcgaaagc agtcacaagc aagaaatcca aggggagag tgatgacttc    4620
catatggact ttgactcagc tgtggctcct cgggcaaaat ctgtacgggc aaagaaacct    4680
ataaagtacc tggaagagtc agatgaagat gatctgtttt aaaatgtgag gcgattattt    4740
taagtaatta tcttaccaag cccaagactg gttttaaagt tacctgaagc tcttaacttc    4800
ctcccctctg aatttagttt ggggaaggtg ttttttagtac aagacatcaa agtgaagtaa    4860
agcccaagtg ttctttagct tttttataata ctgtctaaat agtgaccatc tcatgggcat    4920
tgttttcttc tctgctttgt ctgtgttttg agtctgcttt cttttgtctt taaaacctga    4980
```

| | |
|---|---|
| tttttaagtt cttctgaact gtagaaatag ctatctgatc acttcagcgt aaagcagtgt | 5040 |
| gtttattaac catccactaa gctaaaacta gagcagtttg atttaaaagt gtcactcttc | 5100 |
| ctccttttct actttcagta gatatgagat agagcataat tatctgtttt atcttagttt | 5160 |
| tatacataat ttaccatcag atagaacttt atggttctag tacagatact ctactacact | 5220 |
| cagcctctta tgtgccaagt ttttctttaa gcaatgagaa attgctcatg ttcttcatct | 5280 |
| tctcaaatca tcagaggcca aagaaaaaca ctttggctgt gtctataact tgacacagtc | 5340 |
| aatagaatga agaaaattag agtagttatg tgattatttc agctcttgac ctgtcccctc | 5400 |
| tggctgcctc tgagtctgaa tctcccaaag agagaaacca atttctaaga ggactggatt | 5460 |
| gcagaagact cggggacaac atttgatcca agatcttaaa tgttatattg ataaccatgc | 5520 |
| tcagcaatga gctattagat tcattttggg aaatctccat aatttcaatt tgtaaacttt | 5580 |
| gttaagacct gtctacattg ttatatgtgt gtgacttgag taatgttatc aacgttttg | 5640 |
| taaatattta ctatgttttt ctattagcta aattccaaca attttgtact ttaataaa | 5698 |

<210> SEQ ID NO 4
<211> LENGTH: 894
<212> TYPE: DNA
<213> ORGANISM: Homo sapiens

<400> SEQUENCE: 4

| | |
|---|---|
| atggaagatt ataccaaaat agagaaaatt ggagaaggta cctatggagt tgtgtataag | 60 |
| ggtagacaca aaactacagg tcaagtggta gccatgaaaa aaatcagact agaaagtgaa | 120 |
| gaggaagggg ttcctagtac tgcaattcgg gaaatttctc tattaaagga acttcgtcat | 180 |
| ccaaatatag tcagtcttca ggatgtgctt atgcaggatt ccaggttata tctcatcttt | 240 |
| gagtttcttt ccatggatct gaagaaatac ttggattcta cccctcctgg tcagtacatg | 300 |
| gattcttcac ttgttaagag ttatttatac caaatcctac aggggattgt gttttgtcac | 360 |
| tctagaagag ttcttcacag agacttaaaa cctcaaaatc tcttgattga tgacaaagga | 420 |
| acaattaaac tggctgattt tggccttgcc agagcttttg gaatacctat cagagtatat | 480 |
| acacatgagg tagtaacact ctggtacaga tctccagaag tattgctggg gtcagctcgt | 540 |
| tactcaactc cagttgacat ttggagtata ggcaccatat ttgctgaact agcaactaag | 600 |
| aaaccacttt tccatgggga ttcagaaatt gatcaactct tcaggatttt cagagctttg | 660 |
| ggcactccca taatgaagt gtggccagaa gtggaatctt acaggactta agaatacaca | 720 |
| tttcccaaat ggaaaccagg aagcctagca tcccatgtca aaaacttgga tgaaaatggc | 780 |
| ttggatttgc tctcgaaaat gttaatctat gatccagcca acgaatttc tggcaaaatg | 840 |
| gcactgaatc atccatattt taatgatttg acaatcaga ttaagaagat gtag | 894 |

<210> SEQ ID NO 5
<211> LENGTH: 429
<212> TYPE: DNA
<213> ORGANISM: Homo sapiens

<400> SEQUENCE: 5

| | |
|---|---|
| atgggtgccc cgacgttgcc ccctgcctgg cagcccttc tcaaggacca ccgcatctct | 60 |
| acattcaaga actggcccctt cttggagggc tgcgcctgca ccccggagcg gatggccgag | 120 |
| gctggcttca tccactgccc cactgagaac gagccagact tggcccagtg tttcttctgc | 180 |
| ttcaaggagc tggaaggctg ggagccagat gacgacccca tagaggaaca taaaaagcat | 240 |
| tcgtccggtt gcgctttcct ttctgtcaag aagcagtttg aagaattaac ccttggtgaa | 300 |

| | |
|---|---|
| tttttgaaac tggacagaga aagagccaag aacaaaattg caaaggaaac caacaataag | 360 |
| aagaaagaat tgaggaaac tgcgaagaaa gtgcgccgtg ccatcgagca gctggctgcc | 420 |
| atggattga | 429 |

<210> SEQ ID NO 6
<211> LENGTH: 1314
<212> TYPE: DNA
<213> ORGANISM: Homo sapiens

<400> SEQUENCE: 6

| | |
|---|---|
| atggccttgg ccggggcccc tgcgggcggc ccatgcgcgc cggcgctgga ggccctgctc | 60 |
| ggggccggcg cgctgcggct gctcgactcc tcgcagatcg tcatcatctc cgccgcgcag | 120 |
| gacgccagcg ccccgccggc tcccaccggc cccgcggcgc ccgccgccgg ccctgcgac | 180 |
| cctgacctgc tgctcttcgc cacaccgcag gcgccccggc ccacacccag tgcgccgcgg | 240 |
| cccgcgctcg gccgcccgcc ggtgaagcgg aggctggacc tggaaactga ccatcagtac | 300 |
| ctggccgaga gcagtgggcc agctcggggc agaggccgcc atccaggaaa aggtgtgaaa | 360 |
| tccccggggg agaagtcacg ctatgagacc tcactgaatc tgaccaccaa gcgcttcctg | 420 |
| gagctgctga ccactcggc tgacggtgtc gtcgacctga actgggctgc cgaggtgctg | 480 |
| aaggtgcaga gcggcgcat ctatgacatc accaacgtcc ttgagggcat ccagctcatt | 540 |
| gccaagaagt ccaagaacca catccagtgg ctgggcagcc acaccacagt gggcgtcggc | 600 |
| ggacggcttg agggggttgac ccaggacctc cgacagctgc aggagagcga gcagcagctg | 660 |
| gaccacctga tgaatatctg tactacgcag ctgcgcctgc tctccgagga cactgacagc | 720 |
| cagcgcctgg cctacgtgac cgtgtcaggac cttcgtagca ttgcagaccc tgcagagcag | 780 |
| atggttatgg tgatcaaagc ccctcctgag acccagctcc aagccgtgga ctcttcggag | 840 |
| aactttcaga tctcccttaa gagcaaacaa ggcccgatcg atgttttcct gtgccctgag | 900 |
| gagaccgtag gtgggatcag ccctgggaag accccatccc aggaggtcac ttctgaggag | 960 |
| gagaacaggg ccactgactc tgccaccata gtgtcaccac caccatcatc tcccccctca | 1020 |
| tccctcacca cagatcccag ccagtctcta ctcagcctgg agcaagaacc gctgttgtcc | 1080 |
| cggatgggca gcctgcgggc tcccgtggac gaggaccgcc tgtccccgct ggtggcggcc | 1140 |
| gactcgctcc tggagcatgt gcgggaggac ttctccggcc tctccctga ggagttcatc | 1200 |
| agcctttccc caccccacga ggccctcgac taccacttcg gcctcgagga gggcgagggc | 1260 |
| atcagagacc tcttcgactg tgactttggg gacctcaccc cctggattt ctga | 1314 |

<210> SEQ ID NO 7
<211> LENGTH: 543
<212> TYPE: DNA
<213> ORGANISM: Homo sapiens

<400> SEQUENCE: 7

| | |
|---|---|
| atgggaatcc caatggggaa gtcgatgctg gtgcttctca ccttcttggc cttcgcctcg | 60 |
| tgctgcattg ctgcttaccg ccccagtgag accctgtgcg gcggggagct ggtggacacc | 120 |
| ctccagttcg tctgtgggga ccgcggcttc tacttcagca ggcccgcaag ccgtgtgagc | 180 |
| cgtcgcagcc gtggcatcgt tgaggagtgc tgtttccgca gctgtgacct ggccctcctg | 240 |
| gagacgtact gtgctacccc cgccaagtcc gagagggacg tgtcgacccc tccgaccgtg | 300 |
| cttccggaca acttccccag ataccccgtg ggcaagttct tccaatatga cacctggaag | 360 |

| | |
|---|---|
| cagtccaccc agcgcctgcg caggggcctg cctgccctcc tgcgtgcccg ccggggtcac | 420 |
| gtgctcgcca aggagctcga ggcgttcagg gaggccaaac gtcaccgtcc cctgattgct | 480 |
| ctacccaccc aagaccccgc ccacggggc gccccccag agatggccag caatcggaag | 540 |
| tga | 543 |

<210> SEQ ID NO 8
<211> LENGTH: 4104
<212> TYPE: DNA
<213> ORGANISM: Homo sapiens

<400> SEQUENCE: 8

| | |
|---|---|
| atgaagtctg gctccggagg agggtccccg acctcgctgt gggggctcct gtttctctcc | 60 |
| gccgcgctct cgctctggcc gacgagtgga gaaatctgcg ggccaggcat cgacatccgc | 120 |
| aacgactatc agcagctgaa cgcctggag aactgcacgg tgatcgaggg ctacctccac | 180 |
| atcctgctca tctccaaggc cgaggactac cgcagctacc gcttccccaa gctcacggtc | 240 |
| attaccgagt acttgctgct gttccgagtg gctggcctcg agagcctcgg agacctcttc | 300 |
| cccaacctca cggtcatccg cggctggaaa ctcttctaca actacgccct ggtcatcttc | 360 |
| gagatgacca atctcaagga tattgggctt tacaacctga ggaacattac tcgggggggcc | 420 |
| atcaggattg agaaaaatgc tgacctctgt tacctctcca ctgtggactg gtccctgatc | 480 |
| ctggatgcgg tgtccaataa ctacattgtg ggaataagc ccccaaagga atgtgggac | 540 |
| ctgtgtccag ggaccatgga ggagaagccg atgtgtgaga agaccaccat caacaatgag | 600 |
| tacaactacc gctgctggac cacaaaccgc tgccagaaaa tgtgcccaag cacgtgtggg | 660 |
| aagcgggcgt gcaccgagaa caatgagtgc tgccacccccg agtgcctggg cagctgcagc | 720 |
| gcgcctgaca cgacacggc ctgtgtagct tgccgccact actactatgc cggtgtctgt | 780 |
| gtgcctgcct gcccgcccaa cacctacagg tttgagggct ggcgctgtgt ggaccgtgac | 840 |
| ttctgcgcca catcctcag cgccgagagc agcgactccg aggggtttgt gatccacgac | 900 |
| ggcgagtgca tgcaggagtg cccctcgggc ttcatccgca acggcagcca gagcatgtac | 960 |
| tgcatccctt gtgaaggtcc ttgccccgaag gtctgtgagg aagaaaagaa aacaaagacc | 1020 |
| attgattctg ttacttctgc tcagatgctc caaggatgca ccatcttcaa gggcaatttg | 1080 |
| ctcattaaca tccgacgggg gaataacatt gcttcagagc tggagaactt catgggctc | 1140 |
| atcgaggtgg tgacgggcta cgtgaagatc cgccattctc atgccttggt ctccttgtcc | 1200 |
| ttcctaaaaa accttcgcct catcctagga gaggagcagc tagaagggaa ttactccttc | 1260 |
| tacgtcctcg acaaccagaa cttgcagcaa ctgtgggact gggaccaccg caacctgacc | 1320 |
| atcaaagcag ggaaaatgta ctttgctttc aatcccaaat tatgtgtttc gaaatttac | 1380 |
| cgcatggagg aagtgacggg gactaaaggg cgccaaagca aggggacat aaacaccagg | 1440 |
| aacaacgggg agagagcctc ctgtgaaagt gacgtcctgc atttcacctc caccaccacg | 1500 |
| tcgaagaatc gcatcatcat aacctggcac cggtaccggc cccctgacta cagggatctc | 1560 |
| atcagcttca cccgtttacta caaggaagca ccctttaaga atgtcacaga gtatgatggg | 1620 |
| caggatgcct gcggctccaa cagctggaac atggtggacg tggacctccc gcccaacaag | 1680 |
| gacgtggagc ccggcatctt actacatggg ctgaagcct ggactcagta cgccgtttac | 1740 |
| gtcaaggctg tgacctcac catggtggag aacgaccata tccgtgggc caagagtgag | 1800 |
| atcttgtaca ttcgcaccaa tgcttcagtt ccttccattc ccttggacgt tctttcagca | 1860 |
| tcgaactcct cttctcagtt aatcgtgaag tggaacccctc cctctctgcc aacggcaac | 1920 |

```
ctgagttact acattgtgcg ctggcagcgg cagcctcagg acggctacct ttaccggcac    1980
aattactgct ccaaagacaa aatccccatc aggaagtatg ccgacggcac catcgacatt    2040
gaggaggtca cagagaaccc caagactgag gtgtgtggtg gggagaaagg gccttgctgc    2100
gcctgcccca aaactgaagc cgagaagcag gccgagaagg aggaggctga ataccgcaaa    2160
gtctttgaga atttcctgca caactccatc ttcgtgccca gacctgaaag gaagcggaga    2220
gatgtcatgc aagtggccaa caccaccatg tccagccgaa gcaggaacac cacggccgca    2280
gacacctaca acatcaccga cccggaagag ctggagacag agtaccccttt ctttgagagc    2340
agagtggata caaggagag aactgtcatt tctaaccttc ggcctttcac attgtaccgc    2400
atcgatatcc acagctgcaa ccacgaggct gagaagctgg gctgcagcgc ctccaacttc    2460
gtctttgcaa ggactatgcc cgcagaagga gcagatgaca ttcctgggcc agtgacctgg    2520
gagccaaggc ctgaaaactc catctttta aagtggccgg aacctgagaa tcccaatgga    2580
ttgattctaa tgtatgaaat aaaatacgga tcacaagttg aggatcagcg agaatgtgtg    2640
tccagacagg aatacaggaa gtatggaggg gccaagctaa accggctaaa cccggggaac    2700
tacacagccc ggattcaggc cacatctctc tctgggaatg ggtcgtggac agatcctgtg    2760
ttcttctatg tccaggccaa aacaggatat gaaaacttca tccatctgat catcgctctg    2820
cccgtcgctg tcctgttgat cgtgggaggg ttggtgatta tgctgtacgt cttccataga    2880
aagagaaata acagcaggct ggggaatgga gtgctgtatg cctctgtgaa cccggagtac    2940
ttcagcgctg ctgatgtgta cgttcctgat gagtgggagg tggctcggga gaagatcacc    3000
atgagccggg aacttgggca ggggtcgttt gggatggtct atgaaggagt tgccaagggt    3060
gtggtgaaag atgaacctga aaccagagtg gccattaaaa cagtgaacga ggccgcaagc    3120
atgcgtgaga ggattgagtt tctcaacgaa gcttctgtga tgaaggagtt caattgtcac    3180
catgtggtgc gattgctggg tgtggtgtcc caaggccagc caacactggt catcatggaa    3240
ctgatgacac ggggcgatct caaaagttat ctccggtctc tgaggccaga aatggagaat    3300
aatccagtcc tagcacctcc aagcctgagc aagatgattc agatggccgg agagattgca    3360
gacggcatgg catacctcaa cgccaataag ttcgtccaca gagaccttgc tgcccggaat    3420
tgcatggtag ccgaagattt cacagtcaaa atcggagatt ttggtatgac gcgagatatc    3480
tatgagacag actattaccg gaaagggggg aaagggctgc tgcccgtgcg ctggatgtct    3540
cctgagtccc tcaaggatgg agtcttcacc acttactcgg acgtctggtc cttcggggtc    3600
gtcctctggg agatcgccac actggccgag cagccctacc agggcttgtc caacgagcaa    3660
gtccttcgct tcgtcatgga gggcggcctt ctggacaagc cagacaactg tcctgacatg    3720
ctgtttgaac tgatgcgcat gtgctggcag tataacccca gatgaggcc ttccttcctg    3780
gagatcatca gcagcatcaa agaggagatg agcctggct ccgggaggt ctccttctac    3840
tacagcgagg agaacaagct gcccgagccg gaggagctgg acctggagcc agagaacatg    3900
gagagcgtcc ccctggaccc ctcggcctcc tcgtcctccc tgccactgcc cgacagacac    3960
tcaggacaca aggccgagaa cggccccggc cctggggtgc tggtcctccg cgccagcttc    4020
gacgagagac agccttacgc ccacatgaac ggggccgca agaacgagcg ggccttgccg    4080
ctgccccagt cttcgacctg ctga                                          4104
```

<210> SEQ ID NO 9
<211> LENGTH: 912
<212> TYPE: DNA

<213> ORGANISM: Homo sapiens

<400> SEQUENCE: 9

```
atgagggcct ggatcttctt tctcctttgc ctggccggga gggccttggc agcccctcag        60
caagaagccc tgcctgatga gacagaggtg gtggaagaaa ctgtggcaga ggtgactgag       120
gtatctgtgg gagctaatcc tgtccaggtg gaagtaggag aatttgatga tggtgcagag       180
gaaaccgaag aggaggtggt ggcggaaaat ccctgccaga accaccactg caaacacggc       240
aaggtgtgcg agctggatga aacaacaccc ccatgtgcg tgtgccagga ccccaccagc       300
tgcccagccc ccattggcga gtttgagaag gtgtgcagca atgacaacaa gaccttcgac       360
tcttcctgcc acttctttgc cacaaagtgc accctggagg gcaccaagaa gggccacaag       420
ctccacctgg actacatcgg gccttgcaaa tacatccccc cttgcctgga ctctgagctg       480
accgaattcc ccctgcgcat gcgggactgg ctcaagaacg tcctggtcac cctgtatgag       540
agggatgagg acaacaacct tctgactgag aagcagaagc tgcgggtgaa gaagatccat       600
gagaatgaga agcgcctgga ggcaggagac caccccgtgg agctgctggc ccgggacttc       660
gagaagaact ataacatgta catcttccct gtacactggc agttcggcca gctggaccag       720
caccccattg acgggtacct ctcccacacc gagctggctc cactgcgtgc tcccctcatc       780
cccatggagc attgcaccac ccgctttttc gagacctgtg acctggacaa tgacaagtac       840
atcgccctgg atgagtgggc cggctgcttc ggcatcaagc agaaggatat cgacaaggat       900
cttgtgatct aa                                                           912
```

<210> SEQ ID NO 10
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 10

```
tcgtctccga ggacactgac agcca                                              25
```

<210> SEQ ID NO 11
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 11

```
ggagggcttt tgatcaccat aacca                                              25
```

<210> SEQ ID NO 12
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 12

```
ggagggcttt tgatcaccat aacca                                              25
```

<210> SEQ ID NO 13
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 13
ccgaactgcc agtgtacagg gaaga                                    25

<210> SEQ ID NO 14
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 14
caggaagcct agcatcccat gtc                                      23

<210> SEQ ID NO 15
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 15
ccagaaattc gtttggctgg atc                                      23

<210> SEQ ID NO 16
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 16
cccttggtga atttttgaaa ctgga                                    25

<210> SEQ ID NO 17
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 17
gcactttctc cgcagtttcc tcaaa                                    25

<210> SEQ ID NO 18
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 18
tcctcccctc tgaatttagt ttggg                                    25

<210> SEQ ID NO 19
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 19
aaacaatgcc catgagatgg tcact                                    25

<210> SEQ ID NO 20

```
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 20
ccaagtccga gagggacgtg tcga                                              24

<210> SEQ ID NO 21
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 21
tggaagaact tgcccacggg g                                                 21

<210> SEQ ID NO 22
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 22
ccaacgagca agtccttcgc ttcg                                              24

<210> SEQ ID NO 23
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 23
gggttatact gccagcacat gcgc                                              24
```

METHODS AND KITS USED IN CLASSIFYING ADRENOCORTICAL CARCINOMA

CROSS-REFERENCE TO RELATED APPLICATIONS

This application is a continuation of U.S. patent application Ser. No. 14/807,561, filed Jul. 23, 2015 (published as US 20150329916), which is a continuation of U.S. patent application Ser. No. 13/021,644 filed Feb. 4, 2011 (published as US 20120088681), which claims priority under 35 U.S.C. § 119(e) from U.S. Provisional Application 61/301,826, filed Feb. 5, 2010, entitled MARKERS OF ADRENOCORTICAL CARCINOMA, the contents of each of which are hereby incorporated by reference in their entireties.

REFERENCE TO SEQUENCE LISTING SUBMITTED ELECTRONICALLY

The official copy of the sequence listing is submitted electronically via EFS-Web as an ASCII-formatted sequence listing with a file named "91482_218_Sequence_Listing.txt" created on Apr. 2, 2017, and having a size of 24,662 bytes, and is filed concurrently with the specification. The sequence listing contained in this ASCII-formatted document is part of the specification and is herein incorporated by reference in its entirety.

FIELD OF THE INVENTION

This invention is related to tests that use biomarkers to predict disease outcome. More particularly, the invention is related to tests that use the expression of biomarkers to predict outcome in adrenocortical carcinoma.

BACKGROUND OF THE INVENTION

Adrenocortical carcinoma (ACC) is an aggressive malignancy that forms in the adrenal cortex. ACC generally occurs in adults with a median age of diagnosis at 44 years. ACC is curable when detected early, but because most ACC tumors are still capable of functioning, many patients do not present with endocrine symptoms. As a result, between 40% and 70% of patients have metastatic disease at the time of diagnosis and cannot be cured by surgery. Further, mitotane, the only drug compound approved for treatment of ACC, has severe, dose limiting side effects and only shows a response in approximately 22% of patients. The combination of late diagnosis and ineffective treatments for those with disseminated disease results in an overall 5-year survival rate of 10-20%.

Factors that predict the outcome of a patient's disease are a form of personalized medicine that can inform health care providers about individual patient treatment. Patients likely to have a poorer outcome may have the option of undertaking an aggressive treatment regimen including chemotherapy or experimental treatments. Efforts have been made to seek prognostic factors such as hypo- and hyperdiploidy and expression profiling. While these may be used to manage treatment of ACC patients, they are not a single gene prognostic test. A single gene prognostic test could be more readily adopted by health care providers.

SUMMARY OF THE INVENTION

The invention encompasses a method of predicting the disease outcome of an adrenocortical carcinoma patient on the basis of detecting the expression of a biomarker such as PTTG1 (nucleic acid sequence SEQ ID NO. 1, protein sequence SEQ ID NO. 2). One such disease outcome may be likelihood of survival past a certain date.

In one embodiment of the invention, the patient is classified into a cohort on the basis of protein or DNA expression of PTTG1. In this embodiment, a first reagent capable of binding to either PTTG1 nucleic acid (such as RNA) or protein is added to a mixture that comprises a sample from the patient. The mixture is subjected to conditions that allow detection of the binding of the reagent to the biomarker. The subject may be classified into cohort on the basis of the binding of the reagent to the sample. The cohort may be any cohort, including one or more individuals not likely to survive past a point in time.

In one aspect of this embodiment, the biomarker is PTTG1 protein. In this aspect, the reagent may be an antibody that binds to PTTG1 protein. The antibody may further comprise a label. The label may be any label, including but not limited to a fluorescent compound, an enzyme, or a ligand (such as biotin or streptavidin). Additionally, a second antibody with specificity to the first antibody may be added to the mixture.

In another aspect of this embodiment, the biomarker is a nucleic acid that encodes PTTG1. In this aspect, the reagent may be a nucleic acid complementary to all or part of the marker. The reagent may be any nucleic acid in any form, such as an oligonucleotide. The method may involve adding a second oligonucleotide that binds to part of the marker to the mixture. The first and the second oligonucleotide are constructed to each bind to different parts of the mixture and they each bind to different nucleic acid strands. For example, the first oligonucleotide may bind to the 5'→3' strand while the second oligonucleotide may bind to the 3'→5' strand. The mixture is subjected to nucleic acid amplification, such as PCR. Additionally, a third oligonucleotide may be added to the mixture. The third oligonucleotide is capable of binding to a sequence between the sequences to which the first and second oligonucleotides are capable of binding. The third oligonucleotide may have a label such as a fluorescent label and/or a quencher for the performance of quantitative PCR. The result may be any result that signifies binding such as a band of a certain size visualized through gel electrophoresis or a Ct value. In addition, DNA sequencing may be performed on a product of the nucleic acid amplification.

In another aspect of the invention, the first reagent is affixed to a substrate. In this aspect, a second reagent may be affixed to the substrate and the two reagents are configured to form a microarray.

The sample may be any sample, such as a tumor sample.
The patient may have a tumor belonging to a first tumor cluster.

In another embodiment of the invention, a kit is provided that may be used to classify adrenocortical carcinoma tumors. The kit comprises a reagent capable of binding to either PTTG1 protein or nucleic acid and an indication of a level of expression that signifies the classification of the subject into a cohort, such as a cohort of individuals unlikely to survive past a point in time.

In one aspect of this embodiment, the first reagent comprises a first antibody. The first antibody may further comprise a label. The label may be any label. The kit may comprise a second antibody capable of binding to the first antibody.

In another aspect of this embodiment, the first reagent comprises a nucleic acid. The nucleic acid may be conjugated to a substrate. The nucleic acid may comprise an oligonucleotide. The kit may further comprise a second oligonucleotide and the first and second oligonucleotides are capable of binding to different parts of the marker and to different nucleic acid strands, such as to perform PCR.

In another aspect of this embodiment, the kit may comprise an enzyme. The enzyme may be any enzyme including, for example: a reverse transcriptase, a DNA polymerase, or a thermostable DNA polymerase.

The indication may be any indication of a result that would be used to classify a patient into a cohort such as a positive control or a printed result. The printed result may be any printed result and may include but need not be limited to one or more of the following features either alone or in combination: a Ct value, a range of Ct values, an absorbance value, a fluorescence value, or a photograph. The printed result may be physically included in or on the kit or made available via a website. The indication may also comprise software configured to detect binding of the reagent as input and classification of the subject into the cohort as the output.

It is an object of the invention to provide a test that predicts the disease outcome for adrenocortical carcinoma patients.

It is an object of the invention to provide a test that allows staging of treatment for adrenocortical carcinoma patients.

It is an object of the invention to provide a test that prevents patients from undertaking unnecessary treatments that cause grave side effects.

DESCRIPTION OF THE FIGURES

A more complete understanding of the present invention may be derived by referring to the detailed description when considered in connection with the following illustrative figures.

Figure 1:
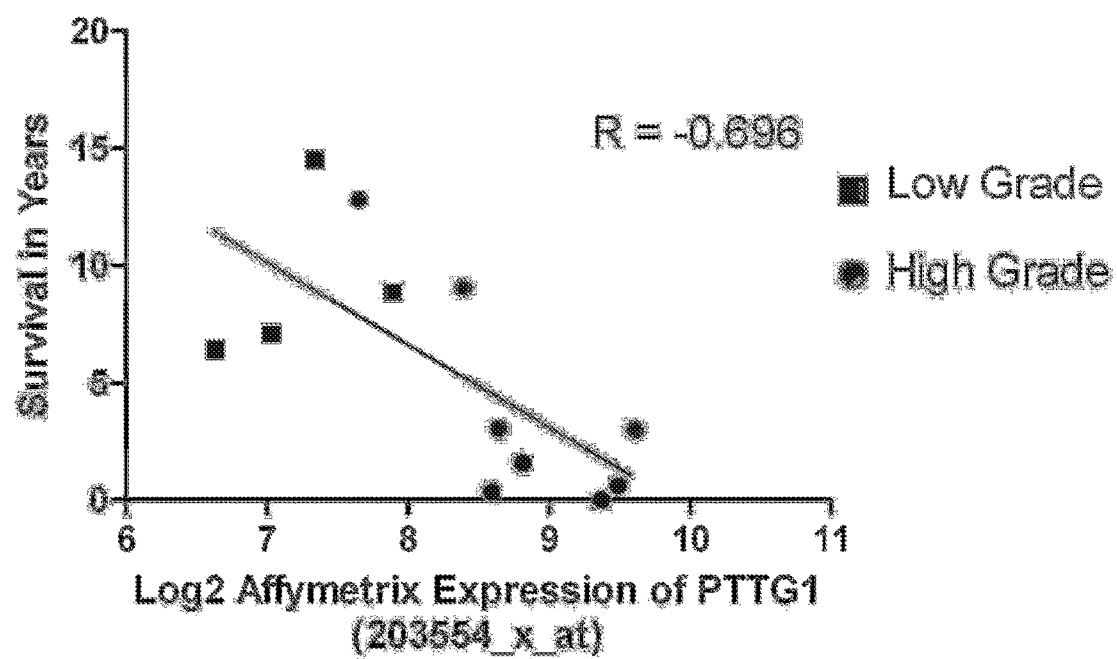
FIG. 1 depicts a scatter plot showing the association of survival with PTTG1 expression. The Pearson's correlation of −0.696 was significant with p=0.012.

Elements and acts in the figures are illustrated for simplicity and have not necessarily been rendered according to any particular sequence or embodiment.

DETAILED DESCRIPTION OF THE INVENTION

In the following description, and for the purposes of explanation, numerous specific details are set forth in order to provide a thorough understanding of the various aspects of the invention. It will be understood, however, by those skilled in the relevant arts, that the present invention may be practiced without these specific details. In other instances, known structures and devices are shown or discussed more generally in order to avoid obscuring the invention. Aspects and applications of the invention presented here are described below in the drawings and detailed description of the invention. Unless specifically noted, it is intended that the words and phrases in the specification and the claims be given their plain, ordinary, and accustomed meaning to those of ordinary skill in the applicable arts.

The invention encompasses methods useful in predicting disease outcome in patients with adrenocortical carcinoma. The methods involve measuring the expression of one or more biomarkers expressed by adrenocortical carcinoma tumors. One such biomarker is any expression product of the human PTTG1 gene, whether nucleic acid (such as DNA or RNA) or protein. The expression of the biomarker may be measured or assessed by any method including any method of measuring RNA or protein. A result of the expression of the biomarker may then be used to predict the outcome of the disease. The outcome may be any outcome, such as survival of the patient past a point in time. The invention also encompasses kits or assemblages of components that may be used to practice the methods. The also kits include an indication of a result that signifies the outcome.

A biomarker may be any molecular structure produced by a cell, expressed inside the cell, accessible on the cell surface, or secreted by the cell. A biomarker may be any protein, carbohydrate, fat, nucleic acid, catalytic site, or any combination of these such as an enzyme, glycoprotein, cell membrane, virus, cell, organ, organelle, or any uni- or multimolecular structure or any other such structure now known or yet to be disclosed whether alone or in combination. A biomarker may also be called a marker and the terms are used interchangeably.

A biomarker may be signified by the sequence of a nucleic acid from which it can be derived, including its DNA, RNA, or protein sequence, or any other sequence, chemical, or structural representation. Examples of nucleic acids that may be biomarkers include miRNA, tRNA, rRNA, siRNA, mRNA, cDNA, or genomic DNA sequences. A biomarker signified by a nucleic acid sequence (such as the sequence of the 5'→3' strand) also includes the complementary sequence (such as the sequence of the 3'→5' strand). A biomarker is not limited to the products of the exact nucleic acid sequence or protein sequence by which it may be represented.

Examples of molecules encompassed by a biomarker represented by a particular sequence or structure include point mutations, silent mutations, deletions, frameshift mutations, translocations, alternative splicing derivatives, differentially methylated sequences, differentially modified protein sequences, truncations, soluble forms of cell membrane associated biomarkers, and any other variation that results in a product that may be identified as the biomarker. The following nonlimiting examples are included for the purposes of clarifying this concept: If expression of a specific biomarker in a sample is assessed by RTPCR, and if the sample expresses an mRNA sequence different from the sequence used to identify the specific biomarker by one or more nucleotides, but the biomarker may still be detected using RTPCR, then the specific biomarker encompasses the sequence present in the sample. Alternatively if expression of a specific biomarker in a sample is assessed by an antibody and the amino acid sequence of the biomarker in the sample differs from a sequence used to identify biomarker by one or more amino acids, but the antibody is still able to bind to the version of the biomarker in the sample, then the specific biomarker encompasses the sequence present in the sample.

A reagent may be any molecule that is capable of specific binding to a biomarker. Reagents thus include but need not be limited to specific nucleic acids, proteins, fats, natural ligands, small molecules, or any other molecule disclosed herein or elsewhere that binds specifically or selectively to a particular biomarker. A reagent may also be a combination or mixture of molecules that binds to one or more biomarkers, such as an antiserum. A reagent may also encompass a set of reagents that specifically binds a set of biomarkers to constitute a biomarker signature.

Expression of a biomarker encompasses any and all processes through which material derived from a nucleic acid template may be produced. Expression thus includes processes such as RNA transcription, mRNA splicing, protein translation, protein folding, post-translational modification, membrane transport, associations with other molecules, addition of carbohydrate moieties to proteins, phosphorylation, protein complex formation and any other process along a continuum that results in biological material derived from genetic material whether in vitro, in vivo, or ex vivo. Expression also encompasses all processes through which the production of material derived from a nucleic acid template may be actively or passively suppressed. Such processes include all aspects of transcriptional and translational regulation. Examples include heterochromatic silencing, transcription factor inhibition, any form of RNAi silencing, microRNA silencing, alternative splicing, protease digestion, posttranslational modification, and alternative protein folding.

Methods used to assess expression of a biomarker include the use of natural or artificial ligands capable of specifically binding a biomarker, particularly a protein biomarker. Such ligands include antibodies, antibody complexes, conjugates, natural ligands, small molecules, nanoparticles, or any other molecular entity capable of specific binding to a biomarker. Antibodies may be monoclonal, polyclonal, or any antibody fragment including an Fab, $F(ab)_2$, Fv, scFv, phage display antibody, peptibody, multispecific ligand, or any other reagent with specific binding to a biomarker. A ligand may be associated with a label such as a radioactive isotope or chelate thereof, a dye (fluorescent or nonfluorescent,) a stain, an enzyme, a metal, or any other substance capable of aiding a detector in differentiating a mixture in which the biomarker is present from a mixture in which the biomarker is absent.

Methods of assessing the expression of protein biomarkers include flow cytometry, immunohistochemistry, ELISA, Western blot, and immunoaffinity chromatography, HPLC, mass spectrometry, protein microarray analysis, PAGE analysis, isoelectric focusing, 2-D gel electrophoresis, or any enzymatic assay. One skilled in the art would understand whether or not a method would require or be enhanced by the use of a specific ligand.

Expression may be assessed by techniques involving nucleic acid amplification. In general, nucleic acid amplification is a process by which copies of a nucleic acid may be made from a source nucleic acid. In some nucleic amplification methods, the copies are generated exponentially. Examples of nucleic acid amplification include but are not limited to: the polymerase chain reaction (PCR), ligase chain reaction (LCR,) self-sustained sequence replication (3SR), nucleic acid sequence based amplification (NASBA,) strand displacement amplification (SDA,) amplification with Qβ replicase, whole genome amplification with enzymes such as φ29, whole genome PCR, in vitro transcription with Klenow or any other RNA polymerase, or any other method by which copies of a desired sequence are generated.

Polymerase chain reaction (PCR) is a particular method of amplifying DNA, generally involving the making of a reaction mixture by mixing a nucleic sample, two or more primers, a DNA polymerase, which may be a thermostable DNA polymerase such as Taq or Pfu, and deoxyribose nucleoside triphosphates (dNTP's). In general, the reaction mixture is subjected to temperature cycles comprising a denaturation stage (typically 80-100° C.) an annealing stage with a temperature that may based on the melting temperature (Tm) of the primers and the degeneracy of the primers, and an extension stage (for example 40-75° C.) The annealing and extension stages may be combined into a single stage. Other stages may also be used depending on the exact PCR method.

Quantitative PCR incorporates a detectable reporter into the reaction mixture in order to quantify the amount of template amplification. The detectable reporter may be, for example, a fluorescent label. The signal from the reporter may be detectable upon incorporation into the amplified DNA as is the case with the SYBR Green molecule. Alternatively, the detectable reporter may be linked to an oligonucleotide probe such as in the case of TaqMan™ quantitative PCR.

The oligonucleotide probe may also comprise a quencher molecule. The quencher hides from detection the majority of the fluorescence that may be emitted by the fluorescent label when the oligonucleotide probe is in solution. PCR amplification removes the quencher from the probe, rendering the fluorescent molecule detectable. Therefore the quantity or intensity of the fluorescence may be correlated with the amount of product formed in the reaction. One skilled in the art would be capable of calculating the amount of target nucleic acid (either DNA or RNA) present in the original reaction mixture from the quantity of the change in fluorescence. Examples of fluorescent labels that may be used in quantitative PCR include but need not be limited to: HEX, TET, 6-FAM, JOE, Cy3, Cy5, ROX, TAMRA, and Texas Red. An oligonucleotide probe used in quantitative PCR may also comprise a quencher. Examples of quenchers that may be used in quantitative PCR include, but need not be limited to TAMRA (which may be used with any of a number of fluorescent labels such as HEX, TET, or 6-FAM), BHQ1, BHQ2, or DABCYL.

An oligonucleotide probe may include any label. A label may be any substance capable of aiding a machine, detector, sensor, device, or enhanced or unenhanced human eye from differentiating a labeled composition from an unlabeled composition. Examples of labels include but are not limited to: a radioactive isotope or chelate thereof, dye (fluorescent or nonfluorescent,) stain, enzyme, or nonradioactive metal. Specific examples include but are not limited to: fluorescein, biotin, digoxigenin, alkaline phosphatese, biotin, streptavidin, $^3$H, $^{14}$C, $^{32}$P, $^{35}$S, or any other compound capable of emitting radiation, rhodamine, 4-(4'-dimethylamino-phenylazo)benzoic acid ("Dabcyl"); 4-(4'-dimethylamino-phenylazo)sulfonic acid (sulfonyl chloride) ("Dabsyl"); 5-((2-aminoethyl)-amino)-naphtalene-1-sulfonic acid ("EDANS"); Psoralene derivatives, haptens, cyanines, acridines, fluorescent rhodol derivatives, cholesterol derivatives; ethylenediaminetetraaceticacid ("EDTA") and derivatives thereof or any other compound that may be differentially detected.

When a nucleic acid such as a primer, oligonucleotide, oligonucleotide probe or any nucleic acid sequence includes a particular sequence, the sequence may be a part of a longer nucleic acid or may be the entirety of the sequence. The nucleic acid that includes the sequence may contain nucleotides 5' of the sequence, 3' of the sequence, or both. The concept of a nucleic acid including a particular sequence further encompasses nucleic acids that contain less than the full sequence that are still capable of specifically hybridizing to the target sequence under any conditions to which a mixture comprising a nucleic acid may be subjected.

A nucleic acid may be identified by the IUPAC letter code which is as follows: A—Adenine base; C—Cytosine base; G—guanine base; T or U—thymine or uracil base. M—A or C; R—A or G; W—A or T; S—C or G; Y—C or T; K—G or T; V—A or C or G; H—A or C or T; D—A or G or T; B—C or G or T; N or X—A or C or G or T. Note that T or U may be used interchangeably depending on whether the nucleic acid is DNA or RNA. A sequence having less than 60% 70%, 80%, 90%, 95%, 99% or 100% identity to the identifying sequence may still be encompassed by the invention if it is able of binding to its complimentary sequence and/or priming nucleic acid amplification of a desired target sequence. If a sequence is represented in degenerate form; for example through the use of codes other than A, C, G, T, or U; the concept of a nucleic acid including the sequence also encompasses a mixture of nucleic acids of different sequences that still meet the conditions imposed by the degenerate sequence.

Reverse transcription PCR is a method of assessing and quantifying RNA expression, particularly mRNA expression, through nucleic acid amplification. Reverse transcription PCR usually involves a reverse transcription process by which a cDNA template is generated from an RNA such as an mRNA. This process is usually accomplished through the use of a reverse transcriptase enzyme.

Other methods of detecting expression of nucleic acid biomarkers include microarray analysis, RNA in situ hybridization, RNAse protection assay, Northern blot, reverse transcriptase treatment followed by direct DNA sequencing, or any other method of detecting a specific nucleic acid now known or yet to be disclosed.

Differential expression encompasses any detectable difference between the expression of a biomarker in one sample relative to the expression of the biomarker in another sample. Differential expression may be assessed in part by a detector. A detector may be any instrument or part of an instrument configured to sense changes in a physical state of a system, including the aided or unaided human eye. Examples of physical states of a system that may change and be sensed by a detector include but need not be limited to fluorescence, absorbance, radiation, sound, color, light, or any other detectable physical property.

Examples of the use of a detector to assess differential expression include but are not limited to: differential staining of cells in an IHC assay configured to detect a biomarker, differential detection of bound RNA on a microarray to which a sequence capable of binding to the biomarker is bound, differential results in measuring RTPCR measured in $\Delta Ct$ or alternatively in the number of PCR cycles necessary to reach a particular optical density at a wavelength at which a double stranded DNA binding dye (e.g. SYBR Green) incorporates, differential results in measuring signal from a labeled probe used in a real-time RTPCR reaction, differential detection of fluorescence on cells using a flow cytometer, differential intensities of bands in a Northern blot, differential intensities of bands in an RNAse protection assay, differential cell death measured by apoptotic biomarkers, differential cell death measured by shrinkage of a tumor, or any method that allows a detection of a difference in signal between one sample or set of samples and another sample or set of samples.

The expression of the biomarker in a sample may be compared to a level of expression predetermined to predict the presence or absence of a particular physiological characteristic. The level of expression may be derived from a single control or a set of controls. A control may be any sample with a previously determined level of expression. A control may comprise material within the sample or material from sources other than the sample. Alternatively, the expression of a biomarker in a sample may be compared to a control that has a level of expression predetermined to signal or not signal a cellular or physiological characteristic. This level of expression may be derived from a single source of material including the sample itself or from a set of sources. Comparison of the expression of the biomarker in the sample to a particular level of expression results in a prediction that the sample exhibits or does not exhibit the cellular or physiological characteristic.

Prediction of a cellular or physiological characteristic includes the prediction of any cellular or physiological state that may be predicted by assessing the expression of a biomarker. Examples include the identity of a cell as a particular cell including a particular normal or cancer cell type, the likelihood that one or more diseases is present or absent, the likelihood that a present disease will progress, remain unchanged, or regress, the likelihood that a disease will respond or not respond to a particular therapy, or any other disease outcome. Further examples include the likelihood that a cell will move, senesce, apoptose, differentiate, metastasize, or change from any state to any other state or maintain its current state.

Expression of a biomarker in a sample may be more or less than that of a level predetermined to predict the presence or absence of a cellular or physiological characteristic. The expression of the biomarker in the sample may be more than 1,000,000×, 100,000×, 10,000×, 1000×, 100×, 10×, 5×, 2×, 1×, 0.5×, 0.1×0.01×, 0.001×, 0.0001×, 0.00001×, 0.000001×, 0.0000001× or less than that of a level predetermined to predict the presence or absence of a cellular or physiological characteristic.

One type of cellular or physiological characteristic is the risk that a particular disease outcome will occur. Assessing this risk includes the performing of any type of test, assay, examination, result, readout, or interpretation that correlates with an increased or decreased probability that an individual has had, currently has, or will develop a particular disease, disorder, symptom, syndrome, or any condition related to health or bodily state or if the person currently has the disease, whether the disease will progress, regress, or remain the same. Examples of disease outcomes include, but need not be limited to survival, death, progression of existing disease, remission of existing disease, initiation of onset of a disease in an otherwise disease-free subject, or the continued lack of disease in a subject in which there has been a remission of disease. Assessing the risk of a particular disease encompasses diagnosis in which the type of disease afflicting a subject is determined. Assessing the risk of a disease outcome also encompasses the concept of prognosis. A prognosis may be any assessment of the risk of disease outcome in an individual in which a particular disease has been diagnosed. Assessing the risk further encompasses prediction of therapeutic response in which a treatment regimen is chosen based on the assessment. Assessing the risk also encompasses a prediction of overall survival after diagnosis.

Determining the level of expression that signifies a physiological or cellular characteristic may be assessed by any of a number of methods. The skilled artisan will understand that numerous methods may be used to select a level of expression for a particular biomarker or a plurality of biomarkers that signifies a particular physiological or cellular characteristic. In diagnosing the presence of a disease, a threshold value may be obtained by performing the assay method on samples obtained from a population of patients having a certain type of disease (cancer for example,) and from a second population of subjects that do not have the disease. In assessing disease outcome or the effect of treatment, a population of patients, all of which have, a disease such as cancer, may be followed for a period of time. After the period of time expires, the population may be divided into two or more groups. For example, the population may be divided into a first group of patients whose disease progresses to a particular endpoint and a second group of patients whose disease does not progress to the particular endpoint. Examples of endpoints include disease recurrence, death, metastasis or other states to which disease may progress. If expression of the biomarker in a sample is more similar to the predetermined expression of the biomarker in one group relative to the other group, the sample may be assigned a risk of having the same outcome as the patient group to which it is more similar.

In addition, one or more levels of expression of the biomarker may be selected that provide an acceptable ability of its ability to signify a particular physiological or cellular characteristic. Examples of such characteristics include identifying or diagnosing a particular disease, assessing a risk of outcome or a prognostic risk, or assessing the risk that a particular treatment will or will not be effective.

For example, Receiver Operating Characteristic curves, or "ROC" curves, may be calculated by plotting the value of a variable versus its relative frequency in two populations. For any particular biomarker, a distribution of biomarker expression levels for subjects with and without a disease may overlap. This indicates that the test does not absolutely distinguish between the two populations with complete accuracy. The area of overlap indicates where the test cannot distinguish the two groups. A threshold is selected. Expression of the biomarker in the sample above the threshold indicates the sample is similar to one group and expression of the biomarker below the threshold indicates the sample is similar to the other group. The area under the ROC curve is a measure of the probability that the expression correctly indicated the similarity of the sample to the proper group. See, e.g., Hanley et al., *Radiology* 143: 29-36 (1982) hereby incorporated by reference.

Additionally, levels of expression may be established by assessing the expression of a biomarker in a sample from one patient, assessing the expression of additional samples from the same patient obtained later in time, and comparing the expression of the biomarker from the later samples with the initial sample or samples. This method may be used in the case of biomarkers that indicate, for example, progression or worsening of disease or lack of efficacy of a treatment regimen or remission of a disease or efficacy of a treatment regimen.

Other methods may be used to assess how accurately the expression of a biomarker signifies a particular physiological or cellular characteristic. Such methods include a positive likelihood ratio, negative likelihood ratio, odds ratio, and/or hazard ratio. In the case of a likelihood ratio, the likelihood that the expression of the biomarker would be found in a sample with a particular cellular or physiological characteristic is compared with the likelihood that the expression of the biomarker would be found in a sample lacking the particular cellular or physiological characteristic.

An odds ratio measures effect size and describes the amount of association or non-independence between two groups. An odds ratio is the ratio of the odds of a biomarker being expressed in one set of samples versus the odds of the biomarker being expressed in the other set of samples. An odds ratio of 1 indicates that the event or condition is equally likely to occur in both groups. An odds ratio grater or less than 1 indicates that expression of the biomarker is more likely to occur in one group or the other depending on how the odds ratio calculation was set up.

A hazard ratio may be calculated by estimate of relative risk. Relative risk is the chance that a particular event will take place. It is a ratio of the probability that an event such as development or progression of a disease will occur in samples that exceed a threshold level of expression of a biomarker over the probability that the event will occur in samples that do not exceed a threshold level of expression of a biomarker. Alternatively, a hazard ratio may be calculated by the limit of the number of events per unit time divided by the number at risk as the time interval decreases. In the case of a hazard ratio, a value of 1 indicates that the relative risk is equal in both the first and second groups. A value greater or less than 1 indicates that the risk is greater in one group or another, depending on the inputs into the calculation.

Additionally, multiple threshold levels of expression may be determined. This can be the case in so-called "tertile," "quartile," or "quintile" analyses. In these methods, multiple groups can be considered together as a single population, and are divided into 3 or more bins having equal numbers of individuals. The boundary between two of these "bins" may be considered threshold levels of expression indicating a particular level of risk of a disease developing or signifying a physiological or cellular state. A risk may be assigned based on which "bin" a test subject falls into.

A subject includes any human or non-human mammal, including for example: a primate, cow, horse, pig, sheep, goat, dog, cat, or rodent, capable of developing cancer including human patients that are suspected of having cancer, that have been diagnosed with cancer, or that have a family history of cancer. Methods of identifying subjects suspected of having cancer include but are not limited to: physical examination, family medical history, subject medical history, endometrial biopsy, or a number of imaging technologies such as ultrasonography, computed tomography, magnetic resonance imaging, magnetic resonance spectroscopy, or positron emission tomography.

The invention contemplates assessing the expression of the biomarker in any biological sample from a subject in which the expression of the biomarker may be assessed. One skilled in the art would know to select a particular biological sample and how to collect said sample depending upon the biomarker that is being assessed. Examples of sources of samples include but are not limited to biopsy or other in vivo or ex vivo analysis of prostate, breast, skin, muscle, facia, brain, endometrium, lung, head and neck, pancreas, small intestine, blood, liver, testes, ovaries, colon, skin, stomach, esophagus, spleen, lymph node, bone marrow, kidney, placenta, or fetus. In some aspects of the invention, the sample comprises a fluid sample, such as peripheral blood, lymph fluid, ascites, serous fluid, pleural effusion, sputum, cerebrospinal fluid, amniotic fluid, lacrimal fluid, stool, or urine. Samples include single cells, whole organs or any fraction of a whole organ, in any condition including in vitro, ex vivo, in vivo, post-mortem, fresh, fixed, or frozen.

In some aspects of the invention, the sample comprises cancer cells. Cancer cells include any cells derived from a tumor, neoplasm, cancer, precancer, cell line, malignancy, or any other source of cells that have the potential to expand and grow to an unlimited degree. Cancer cells may be derived from naturally occurring sources or may be artificially created. Cancer cells may also be capable of invasion into other tissues and metastasis. Cancer cells further encompass any malignant cells that have invaded other tissues and/or metastasized. One or more cancer cells in the context of an organism may also be called a cancer, tumor, neoplasm, growth, malignancy, or any other term used in the art to describe cells in a cancerous state.

Examples of cancers that could serve as sources of cancer cells include solid tumors such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma.

Additional cancers that may serve as sources of cancer cells include blood borne cancers such as acute lymphoblastic leukemia ("ALL,"), acute lymphoblastic B-cell leukemia, acute lymphoblastic T-cell leukemia, acute myeloblastic leukemia ("AML"), acute promyelocytic leukemia ("APL"), acute monoblastic leukemia, acute erythroleukemic leukemia, acute megakaryoblastic leukemia, acute myelomonocytic leukemia, acute nonlymphocytic leukemia, acute undifferentiated leukemia, chronic myelocytic leukemia ("CML"), chronic lymphocytic leukemia ("CLL"), hairy cell leukemia, multiple myeloma, lymphoblastic leukemia, myelogenous leukemia, lymphocytic leukemia, myelocytic leukemia, Hodgkin's disease, non-Hodgkin's Lymphoma, Waldenstrom's macroglobulinemia, Heavy chain disease, and Polycythemia vera.

The present invention further provides kits to be used in assessing the expression of a biomarker in a subject to predict disease outcome. Kits include any combination of components that facilitates the performance of an assay. A kit that facilitates assessing the expression of an RNA may include suitable nucleic acid-based and immunological reagents as well as suitable buffers, control reagents, and printed protocols.

Kits that facilitate nucleic acid based methods may further include one or more of the following: specific nucleic acids such as oligonucleotides, labeling reagents, enzymes including PCR amplification reagents such as Taq or Pfu, reverse transcriptase, or one or more other polymerases, and/or reagents that facilitate hybridization. Specific nucleic acids may include nucleic acids, polynucleotides, oligonucleotides (DNA, or RNA), or any combination of molecules that includes one or more of the above, or any other molecular entity capable of specific binding to a nucleic acid biomarker. In one aspect of the invention, the specific nucleic acid comprises one or more oligonucleotides capable of hybridizing to the biomarker.

An oligonucleotide may be any polynucleotide of at least 2 nucleotides. Oligonucleotides may be less than 10, less than 15, less than 20, less than 30, less than 40, less than 50, less than 75, less than 100, less than 200, more than 200 or more than 500 nucleotides in length. While oligonucleotides are often linear, they may, depending on their sequence and conditions, assume a two- or three-dimensional structure. Oligonucleotides may be chemically synthesized by any of a number of methods including sequential synthesis, solid phase synthesis, or any other synthesis method now known or yet to be disclosed. Alternatively, oligonucleotides may be produced by recombinant DNA based methods. One skilled in the art would understand the length of oligonucleotide necessary to perform a particular task. Oligonucleotides may be directly labeled, used as primers in PCR or sequencing reactions, or bound directly to a solid substrate as in oligonucleotide arrays.

In some aspects of the invention, the probe may be affixed to a solid substrate. In other aspects of the invention, the sample may be affixed to a solid substrate. A probe or sample may be covalently bound to the substrate or it may be bound by some non covalent interaction including electrostatic, hydrophobic, hydrogen bonding, Van Der Waals, magnetic, or any other interaction by which a probe such as an oligonucleotide probe may be attached to a substrate while maintaining its ability to recognize the allele to which it has specificity. A substrate may be any solid or semi solid material onto which a probe may be affixed, attached or printed, either singly or in the formation of a microarray. Examples of substrate materials include but are not limited to polyvinyl, polysterene, polypropylene, polyester or any other plastic, glass, silicon dioxide or other silanes, hydrogels, gold, platinum, microbeads, micelles and other lipid formations, nitrocellulose, or nylon membranes. The substrate may take any form, including a spherical bead or flat surface. For example, the probe may be bound to a substrate in the case of an array. The sample may be bound to a substrate as (for example) the case of a Southern Blot, Northern blot or other method that affixes the sample to a substrate.

Kits may also contain reagents that detect proteins, often through the use of an antibody. These kits will contain one or more specific antibodies, buffers, and other reagents configured to detect binding of the antibody to the specific epitope. One or more of the antibodies may be labeled with a fluorescent, enzymatic, magnetic, metallic, chemical, or other label that signifies and/or locates the presence of specifically bound antibody. The kit may also contain one or more secondary antibodies that specifically recognize epitopes on other antibodies. These secondary antibodies may also be labeled. The concept of a secondary antibody also encompasses non-antibody ligands that specifically bind an epitope or label of another antibody. For example, streptavidin or avidin may bind to biotin conjugated to another antibody. Such a kit may also contain enzymatic substrates that change color or some other property in the presence of an enzyme that is conjugated to one or more antibodies included in the kit.

A kit may also contain an indication of a level of expression that signifies a particular physiological or cellular characteristic. An indication includes any guide to a level of expression that, using the kit in which the indication is provided, would signal the presence or absence of any physiological or cellular state that the kit is configured to detect. The indication may be expressed numerically, expressed as a color, expressed as an intensity of a band, derived from a standard curve, or derived from a control. The indication may be in the form of a printed result that may be included in the kit or it may be posted on a website or embedded in a software package.

Elements and acts in the example are intended to illustrate the invention for the sake of simplicity and have not necessarily been rendered according to any particular sequence or embodiment. The example is also intended to establish possession of the invention by the Inventors.

EXAMPLES

Example 1

Identification of Genes Expressed in the G2/M Phase as Potential Biomarkers of Outcome in ACC Previous gene expression studies have focused on identifying gene expression signatures that differentiate ACC from benign adrenal adenomas and normal adrenal tissue (See References 5, 6, 8, 9, 15, and 16). IGF2, FGFR1, FGFR2, FGFR4, and TOP2A have been shown to have a greater degree of expression in ACC while CDKN1C, KCNQ1, ADH1, IGFBP6, IGFR1, and ABCB1 show decreased expression in ACC (See References 9, 15, and 18). A panel of genes related to IGF2 signaling and steroidogenesis is almost as good as the Weiss score at predicting recurrence (See Reference 5) and two additional studies have shown that ACC can be subdivided into two groups with differences in survival based on gene expression profiles. (See References 6 and 8). A two-gene signature, PINK1 and BUB1B has been shown to be associated with poor prognosis (See Reference 6).

Expression profiling was performed on 20 ACC tumors on two complementary platforms: the Affymetrix U133 Plus 2 and the Agilent 22K Human Genome microarray. Analysis of data from both platforms identified ubiquitination and cell-cycle progression through G2/M as pathways that are significantly dysregulated in ACC. Furthermore, several genes involved in the dysregulation of the G2/M transition are expressed in a similar pattern as CDC2 (expressed when CDC2 expression is also expressed.) Hierarchical clustering using sets of genes that were expressed in a similar or disparate (expressed when CDC2 expression is suppressed) pattern as CDC2 allowed grouping of ACC tumors by histological grade. Perturbations of the IGF2-IGF1R signaling pathway beyond expression of IGF2 are an early event present in low-grade tumors, as are perturbations of the p53 pathway. Dysregulation of E2F family members, particularly E2F1 and E2F4, were also observed, even when the expression of cell cycle related genes were taken into account. Further, over-expression of PTTG1, a gene that links the G2/M transition and p53 pathway was shown to be a biomarker of poor survival.

Clinical Samples

A total set of 30 ACC flash frozen tumors and 4 normal adrenal glands were collected at the Mayo Clinic in Rochester, Minn., the University Hospital Essen (Essen, Germany) and the University of Calgary (Alberta, Canada). Research consent was obtained under the WIRB approved protocol #20051769. Tumor histological grade was determined using the Weiss criteria of adrenocortical carcinomas. (See Reference 17).

Expression Analysis

RNA was extracted from 100 mg samples of 30 ACC tumors and 4 normal adrenal tissues, amplified and reverse-transcribed with biotin labeled nucleotides. Biotin-labeled cRNA was synthesized and purified using cRNA filter cartridges. Labeled cRNA was fragmented and hybridized to Affymetrix U133 Plus 2 human genome arrays following the manufacturer's protocol. Scanning and washing was completed on a Fluidic Stations FS450 and a GeneChip® Scanner 3000 with Workstation.

RNA from 15 of the above 30 tumors and normal total adrenal glands was reverse transcribed, amplified and labeled with a fluorescent nucleotide (Cy5 for tumors and Cy3 for normal adrenals). The labeled cRNAs were then co-hybridized to Agilent 22K human genome chips following manufacturer's protocols. The arrays were scanned, and the resulting TIF files were subject to feature extraction using the Agilent FE8.1.

Statistical Analysis

Affymetrix data quality was assessed using the affyQCReport package in Bioconductor. Agilent data quality was accessed using the arrayQuality software package. Nineteen of the Affymetrix chips passed quality control, and all Agilent chips passed, leading to a total of 20 tumors with data, 14 of which have data from both platforms. The Affymetrix data was normalized by RMA. Agilent data was processed similarly using the mArray and Limma software packages. Controls were removed from the Agilent dataset and minimum background subtracted. This data was then normalized within arrays using the median values across the probes and normalized across arrays using quantile normalization. In both the datasets differentially expressed genes were identified using a linear model with fixed effects. A non-intercept model was used to determine the differences between tumor and normal samples. Positive B-Statistics was used to distinguish the set of differentially expressed genes.

RT-PCR Validation

Total RNA was reverse transcribed utilizing random hexamer primers and a cDNA synthesis kit. The resulting cDNA was amplified with SYBR green and gene specific primers designed to span the closest intron-exon junction of the reference sequence to which the probes on the array were designed (See Table 1). The cDNA was amplified using a 50° C. preheat step for 2 min., a 95° C. heat activation step for 2 min., followed by 40 cycles of denaturation at 95° C. for 15 sec., annealing at the temperature in Table 1 for 30 sec., and elongation at 72° C. for 30 seconds. Melting curve analysis was performed to evaluate primer set specificity. Beta-actin was used as the reference gene. Fold difference in cDNA concentration was calculated using the Pfaffl method taking into account reaction efficiencies (See Reference 14).

Pathway Analysis

Pathway analysis identified cellular pathways with significant over-representation within the ACC versus normal tissue dataset. Affymetrix and Agilent data sets were each analyzed using both the Interactome Analysis in GeneGo and by Gene Set Enrichment Analysis using curated gene sets corresponding to Gene Ontology categories. Data sets included differentially expressed genes, genes showing a 2 fold or greater change in expression or other expression changes as detailed in the results.

Transcriptional Regulation Analysis

Cell cycle genes showing correlated expression ($r \geq |0.7|$) with CDC2 were examined for common transcriptional elements in their promoters. These cell cycle associated genes were assessed for consensus promoter regions within the genomic sequence. Common transcriptional elements were cataloged. Additionally, the promoter sequences of the correlated genes up to 1000 bp up-stream of the transcriptional start site were parsed with a natural language algorithm. The most common fragment size was then analyzed for sequence content and compared to the sequence of known transcription factor binding sites. Finally, the Interactome analysis of GeneGo was used to identify transcription factors showing over-representation for both the Affymetrix and Agilent data considered together for differentially expressed genes, genes showing a 2-fold or greater change in expression, and genes differentially expressed or with a 2-fold or greater change in expression stratified by tumor grade. For example, low-0 grade tumors (grades 1 and 2) may be analyzed independently from high-grade tumors (grades 3 and 4).

Flow Cytometry

Nuclei were isolated from frozen tissue and sorted on the basis of DAPI fluorescence for DNA content as previously described. (See Reference 13.)

Analysis of the data from both the Affymetrix U133 Plus 2 platform and the Agilent 22K microarray platform identified several genes that display differential expression when expression of the genes in ACC is compared to non-diseased adrenal tissue. Differentially expressed genes include genes involved in IGF2 signaling, including IGF1R, IGFBP5, and IGFBP6, and TOP2A. IGF2 is over-expressed relative to normal adrenal by an average of 2.4 fold in the Affymetrix data and 1.71 fold in the Agilent data. H19 and CDKN1C (p57$^{kip}$) were found to be differentially under-expressed in ACC relative to normal adrenal. RT-qPCR validation of two normal adrenal samples, three low-grade ACC and three high-grade ACC was performed for a selection of genes including IGF2 (Table 1 for primers, Table 3 for results). Analysis of IGF2 confirmed over-expression, in high-grade tumors showing greater increases in expression.

Hierarchical clustering of genes shown to be differentially expressed in both platforms allowed differentiation of normal from tumor and additionally allowed differentiation of tumors of grades 1 and 2 from tumors of grades 3 and 4. (Table 2) Independent gene ontology enrichment analysis on both the Affymetrix and Agilent data sets showed that differentially expressed genes fell into cell cycle control and ubiquitination pathways. Interactome analysis was used to find further differences between ACC and normal adrenals. When the interactome of genes identified as differentially expressed by both platforms was analyzed, there was a connection to the E2F transcription factors, particularly E2F1 and E2F4, as well as p53. Kinases that arose from the interactome analysis were primarily centered on cell cycle control, raf, and ERK. There was also evidence of perturbations in chromatin remodeling because both p300 and HDAC1 were identified as over-connected (Table 3).

Gene Set Enrichment Analysis (GSEA) on the Affymetrix-derived data set using curated gene sets relating to Gene Ontology categories yields a rank ordering of the genes between classes. Upon inspection of the top 50 ranked genes differentially expressed in normal adrenal and the top 50 ranked genes differentially expressed in ACC, the genes with the greatest degree of differential expression in normal adrenal relative to ACC are all under-expressed in ACC. This underexpression is independent of tumor grade. The genes with the greatest degree of overexpression in ACC relative to normal adrenal are differentially expressed with regard to tumor grade—specifically, high-grade tumors (pathological grade 3 and grade 4) may be distinguished from low-grade (grades 1 and 2). GSEA for normal adrenal as compared to ACC yielded no significant enrichment in the normal samples. GSEA for ACC demonstrated enrichment in the chromosome organization and biogenesis set. Leading edge analysis demonstrated that the enrichment in ACC was being driven by TP53, MDM2, and RAD51 expression (Table 2). Differential expression in normal adrenal was driven by CCL2, ADORA2A, and CXCL1. Many of the genes that are overexpressed in ACC are part of the chromosome instability expression cassette (See Reference 3). As a result, these genes were filtered out of the analysis. A re-run of the GSEA analysis after this filtering increased the gene sets for ACC as a whole with only chromosome organization and biogenesis remaining the same (Table 3). TP53 and MDM2 continued to drive the enrichment in gene sets regardless of tumor grade.

Analyzing a list of genes from GO category enrichment refined the cell cycle enrichment category to the G2/M transition and mitosis subcategory. GeneGo interactome analysis highlighted the involvement of the E2F transcription factors, p53, c-myc, FOXM1, and SP1 among others. Over-connected kinases, phosphatases, enzymes, and other proteins were centered on the G2/M and S-phase transitions of the cell cycle, DNA repair, and JNK signaling.

The genes used in the GeneGo analyses were expanded to include those that may not be differentially expressed but exhibited a ≥2-fold change in expression in either direction as compared to normal adrenals. GeneGo interactome analysis by tumor grade revealed that very little was over-connected when looking at genes that were over-expressed 2 fold or greater in low grade tumors but several proteins were over-connected among when looking at genes with a 2 fold or greater reduction in expression. Both IGF1 and NOV, ligands for IGF1R, were identified and are also under expressed as was IGFBP5, a negative regulator of IGF2 function. Additionally, there was evidence of dysregulation of TGF-β signaling and extra-cellular matrix modulations. These results held when the CIN70 genes were removed. High grade tumors had similar results for under-expressed genes. However, when looking at over-expressed genes, there were considerably more genes showing over-connection. Of particular note was the inclusion of not only proteins involved in cell cycle control, but DNA repair.

Figure 2:
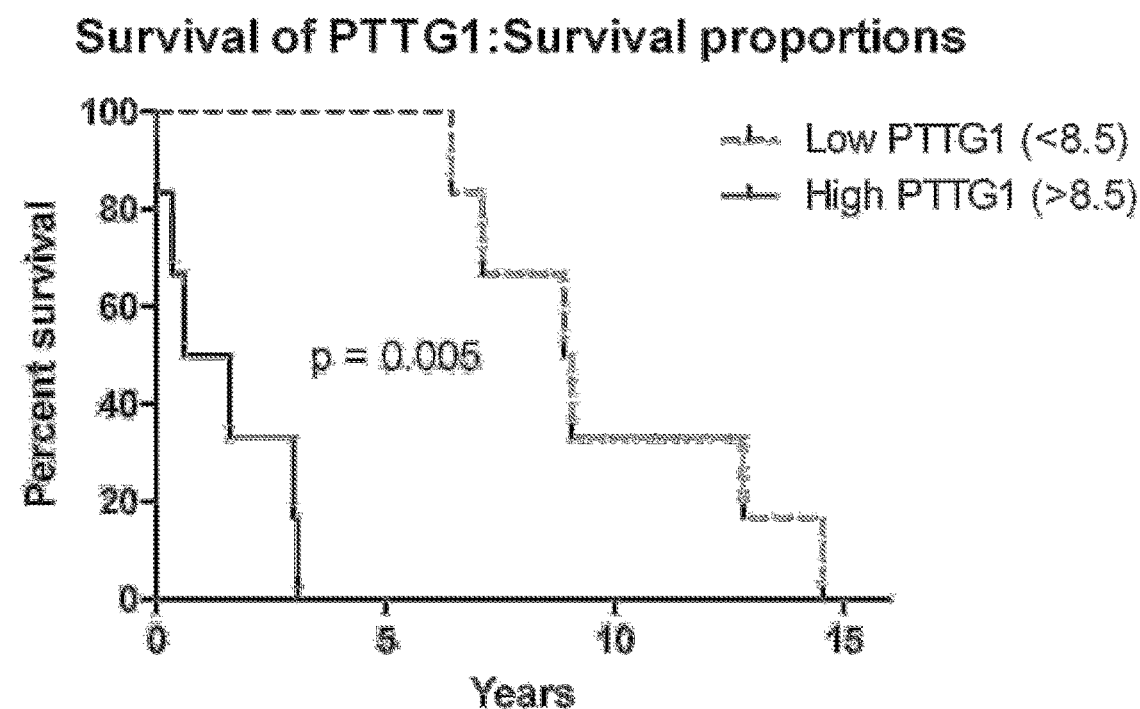
FIG. 2 depicts a survival curves between tumors with high (>8.5 on the Affymetrix array) or low (<8.5 on the Affymetrix array) PTTG1 expression. The cut-off of 8.5 represents the median expression value for PTTG1 across all samples.

The identification of the cell cycle in general and G2/M in particular as biological processes enriched both the normal adrenal to ACC comparison and the comparisons based on tumor grade led to a focus on CDC2 expression—specifically, genes that did not meet the criteria set for differential expression but were overexpressed when CDC2 was overexpressed or underexpressed when CDC2 was underexpressed or underexpressed when CDC2 was overexpressed in ACC relative to normal. A correlation analysis demonstrated both positive and negative correlations of CDC2 to other genes (Table 4). The genes resulting from this analysis were also able to differentiate tumors by grade. Since the differentiation correlates with grade and since grade correlates with survival, the expression of the genes included in the CDC2 correlated gene set was assessed to determine association with survival. PTTG1 was the sole gene that allowed differentiation of tumors on the basis of survival. Increased expression of this gene relative to a normal controls corresponded to decreased survival (FIGS. 1 and 2).

Example 2

PTTG1 is a Biomarker of Decreased Survival in ACC

PTTG1 encodes the protein securin. Securin is involved in the G2/M transition of the cell cycle by inhibiting the activity of separase through phosophorylation. It is degraded by the anaphase-promoting complex, releasing the inhibition of separase and promoting sister chromatid separation. Securin has also been implicated in the negative regulation of p53 through phosphorylation of p53.

PTTG1 was identified as a target of interest through expression profiling of 20 ACC tumor samples. PTTG1 was identified as differentially over-expressed 3-5 fold on both the Affymetrix U133 Plus 2 and the Agilent Human 1A Oligo Microarray (v2) platforms. Analysis of that data identified the G2/M transition, particularly sister chromatid separation, as being dysregulated. One such gene that showed coordinate expression with CDC2 was PTTG1. PTTG1 was the sole gene tested to show a significant association between the level of expression and survival (FIG. 1). A level of expression of 8.5, the median value of expression data from the Affymetrix platform over 19 samples, was used to segregate patients into cohorts. The cohort of patients with a PTTG1 expression value over 8.5 showed significantly poorer survival than the cohort of patients with an expression value less than 8.5 (FIG. 2).

The promoter sequences of the genes correlated with CDC2 expression were analyzed up to 1000 bp up-stream of the transcriptional start site using a natural language algorithm. The most common fragment size was then analyzed for sequence content and compared to the sequence of known transcription factor binding sites. This analysis yielded the binding site for E2F1-Dp1. Using a complementary approach, binding site matrices of the promoters from the correlated genes were analyzed for common transcription factor binding sites. Again, the analysis identified consensus binding site for E2F1.

Example 3

Figure 3:
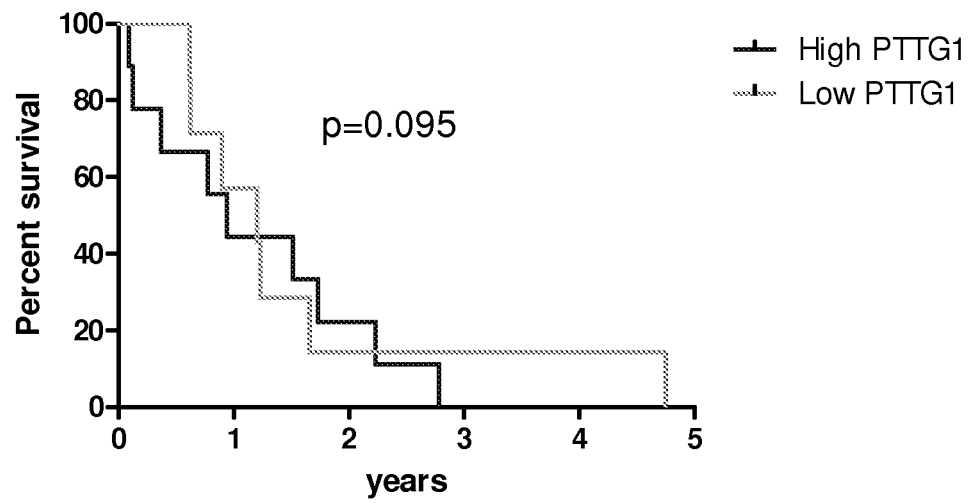
FIG. 3 depicts the level of expression of PTTG1 in data from Giordano T J et al, Clin Cancer Res 15, 668-676 (2009) relative to survival.
Figure 4:
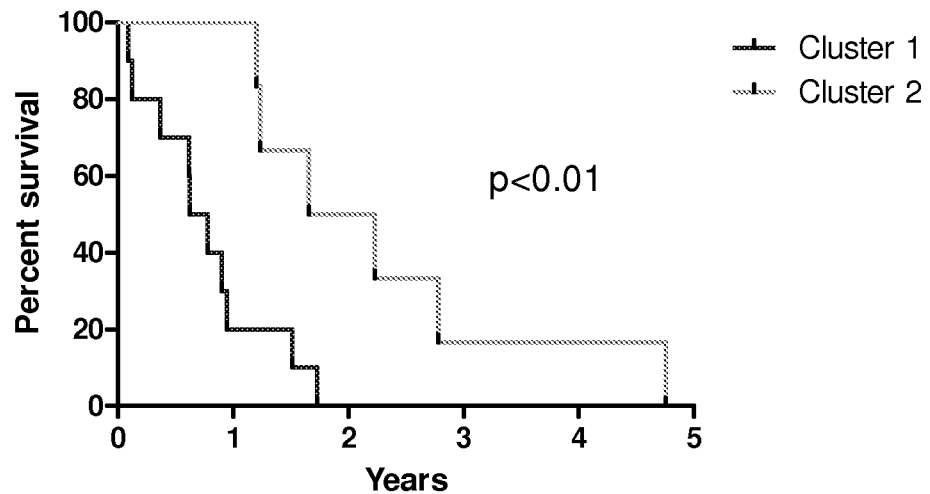
FIG. 4 depicts data from Giordano T J et al, Clin Cancer Res 15, 668-676 (2009) displaying different survival clusters reported in that reference.
Figure 5:
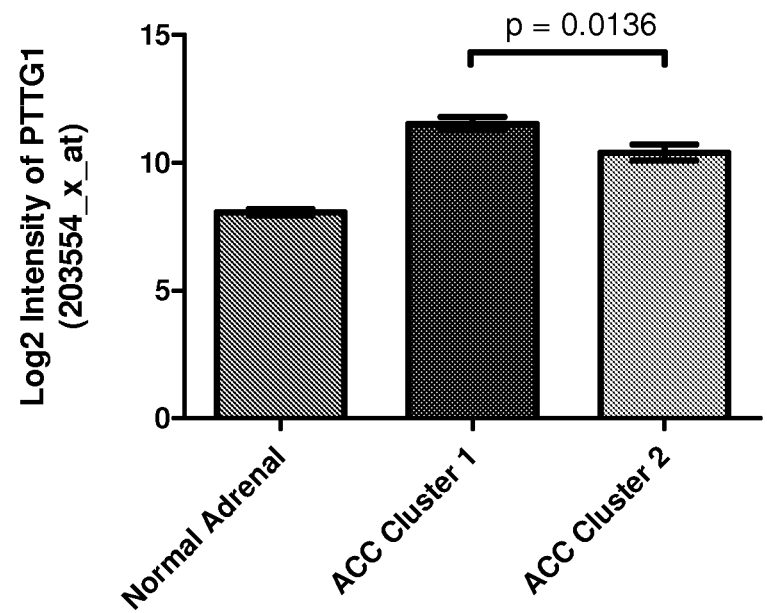
FIG. 5 depicts a significant difference between the expression of PTTG1 in ACC tumor cluster 1 from FIG. 4 (low survival) the expression of PTTG1 in ACC tumor cluster 2 (better survival.)

PTTG1 Expression Correlates with a Cluster of ACC Tumors Likely to have Poor Survival Examination of data from Giordano T J et al, Clin Cancer Res 15, 668-676 (2009) showed that expression of PTTG1 did not significantly correlate with survival and therefore teaches away from this invention (FIG. 3). Giordano does report the presence of ACC tumor clusters. FIG. 4 shows that tumors classified as Cluster 1 have a poor survival outcome. Tumors classified as Cluster 2 have a better survival outcome. While PTTG1 expression does not directly correlate with survival, PTTG1 does directly correlate with cluster expression. FIG. 5 shows that tumor cluster 1 has higher PTTG1 expression than tumor cluster 2.

Example 4

Vorinostat Decreases PTTG1 Expression

Figure 6:
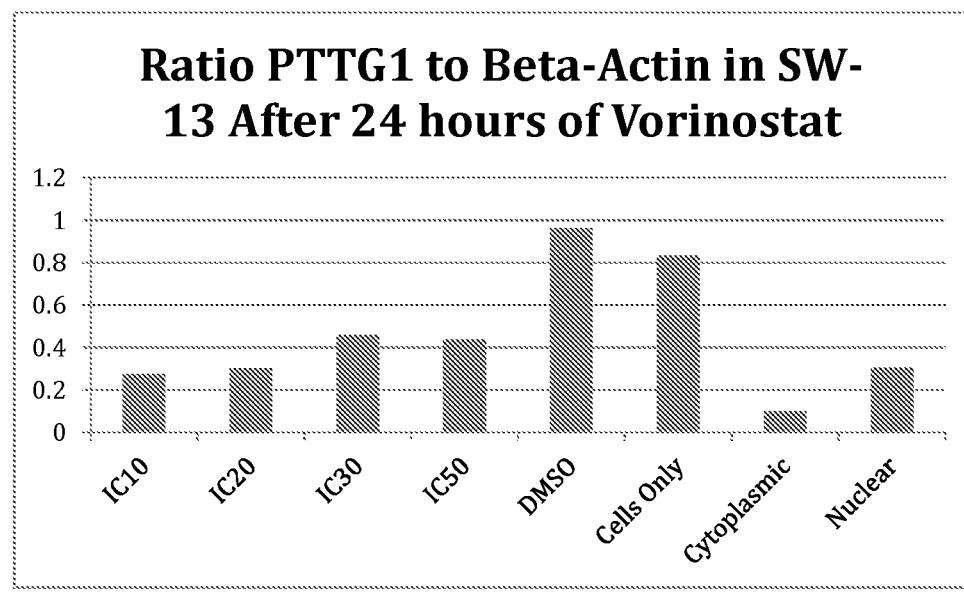
FIG. 6 depicts the effect of vorinostat on the ACC cell line SW-13. Vorinostat reduces PTTG1 expression in SW13 cells.
Figure 7:
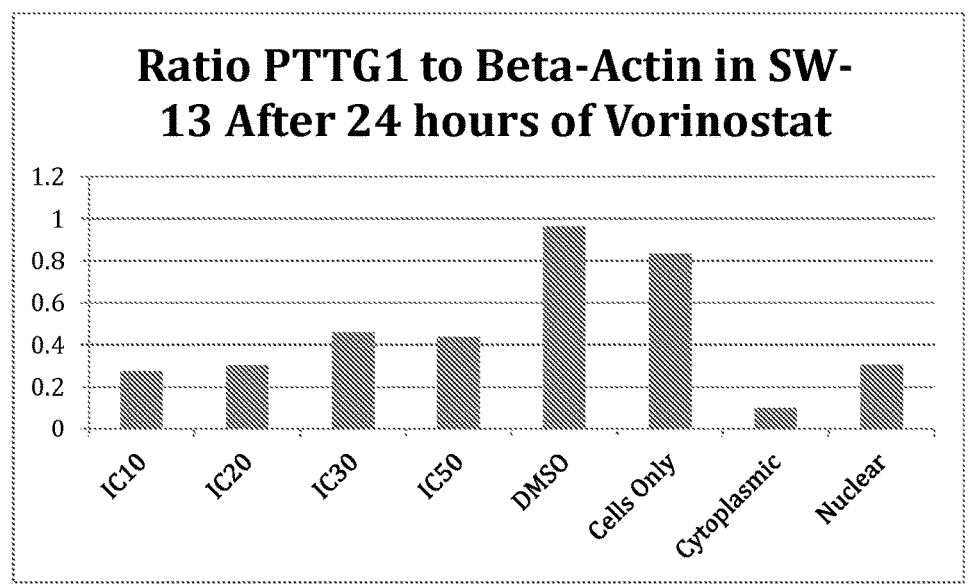
FIG. 7 depicts the effect of vorinostat on the ACC cell line H259R. Vorinostat reduces PTTG1 expression in H259R cells.

Small molecule inhibitors that directly inhibit PTTG1 are unavailable. Vorinostat is a selective inhibitor of HDAC1, HDAC2, HDAC3, and HDAC6. FIGS. 6 and 7 show that vorinostat reduces PTTG1 expression in both the SW-13 and H259R ACC cell lines. In the figures, expression of PTTG1 is shown relative to the expression of beta-actin. Vorinostat reduces SW-13 cell viability by 50% at a 1.7 µM concentration. It also reduces H295R viability by 50% at a 0.9 µM.

REFERENCES

So as to reduce the complexity and length of the Detailed Specification, Inventor(s) herein expressly incorporate(s) by reference to the extent allowed all of the following materials.

1. Barlaskar F M et al, *J Clin Endocrinol Metab* 94, 204-212 (2009).
2. Blake J A et al, Nucleic Acids Res 37, D712-D719 (2009).
3. Carter S L et al, Nat Genet 38, 1043-1048 (2006).
4. Cohn K et al, Surgery 100, 1170-1177 (1986).
5. de Fraipont F et al, J Clin Endocrinol Metab 90, 1819-1829 (2005).
6. de Reynies A et al, J Clin Oncol 27, 1108-1115 (2009).
7. Decker R A et al, Surgery 110, 1006-1013 (1991).
8. Giordano T J et al, Clin Cancer Res 15, 668-676 (2009).
9. Giordano T J et al, Am J Pathol 162, 521-531 (2003).
10. Ignaszak-Szczepaniak M et al, Oncol Rep 16 65-71 (2006).
11. Laurell C et al, Eur J Endocrinol 161, 141-152 (2009).
12. Lee J E et al, Surgery 118, 1090-1098 (1995).
13. Paulson T G, Genome Res 9, 482-491 (1999).
14. Pfaffl M W Nucleic Acids Res 29, e45 (2001).
15. Slater E P, Eur J Endocrinol 154, 587-598 (2006).
16. Velazquez-Fernandez D, Surgery 138, 1087-1094, (2005).
17. Weiss L M, Am J Surg Pathol 8, 163-169 (1984).
18. West A N et al, Cancer Res 67, 600-608 (2007).
19. R Development Core Team (2008). R: A language and environment for statistical computing. R Foundation for Statistical Computing, Vienna, Austria. ISBN 3-900051-07-0, URL: http://www.R-project.org.
20. Gentleman R C, et al. Genome Biol 5, R80 (2004

TABLES

TABLE 1

PCR Primers

| Biomarker | Direction | Sequence | Annealing Temp | SEQ ID NO |
|---|---|---|---|---|
| E2F1 | Forward | TCGTCTCCGAGGACAC TGACAGCCA | 59 | SEQ ID NO. 8 |
| E2F1 | Reverse | GGAGGGGCTTTGATCA CCATAACCA | 59 | SEQ ID NO. 9 |
| SPARC | Forward | TCTGACTGAGAAGCAG AAGCTGCGG | 62 | SEQ ID NO. 10 |
| SPARC | Reverse | CCGAACTGCCAGTGTA CAGGGAAGA | 62 | SEQ ID NO. 11 |
| CDC2 | Forward | CAGGAAGCCTAGCATC CCATGTC | 59 | SEQ ID NO. 12 |
| CDC2 | Reverse | CCAGAAATTCGTTTGG CTGGATC | 59 | SEQ ID NO. 13 |
| BIRC5 | Forward | CCCTTGGTGAATTTTT GAAACTGGA | 59 | SEQ ID NO. 14 |
| BIRC5 | Reverse | GCACTTTCTCCGCAGT TTCCTCAAA | 59 | SEQ ID NO. 15 |
| TOP2A | Forward | TCCTCCCCTCTGAATT TAGTTTGGG | 62 | SEQ ID NO. 16 |
| TOP2A | Reverse | AAACAATGCCCATGAG ATGGTCACT | 62 | SEQ ID NO. 17 |
| IGF2 | Forward | CCAAGTCCGAGAGGGA CGTGTCGA | 59 | SEQ ID NO. 18 |
| IGF2 | Reverse | TGGAAGAACTTGCCCA CGGGG | 59 | SEQ ID NO. 19 |

TABLE 1-continued

PCR Primers

| Biomarker | Direction | Sequence | Annealing Temp | SEQ ID NO |
|---|---|---|---|---|
| IGF1R | Forward | CCAACGAGCAAGTCCTTCGCTTCG | 59 | SEQ ID NO. 20 |
| IGF1R | Reverse | GGGTTATACTGCCAGCACATGCGC | 59 | SEQ ID NO. 21 |

TABLE 2

Expression relative to normal adrenal of selected genes in ACC samples. Samples are sorted according to grade.

| | ACC sample number | E2F1 | SPARC | CDC2 | BIRC5 | TOP2A | IGF2 | IGF1R |
|---|---|---|---|---|---|---|---|---|
| low grade | 7 | 8.53*** | 2.93*** | 15.10**** | 7.25*** | 570.39***** | 7.79*** | 1.84** |
| | 27 | 12.71**** | 3.12*** | 23.29**** | 23.28**** | 534.85***** | 16.54**** | 0.58* |
| | 28 | 10.46**** | 1.53** | 54.12**** | 44.28**** | 576.73***** | 10.60**** | 1.06** |
| high grade | 10 | 42.50**** | 0.06* | 160.09***** | 334.35***** | 763.03***** | 32.83**** | 2.04*** |
| | 12 | 11.11**** | 2.05*** | 46.12**** | 73.44**** | 815.97***** | 12.52**** | 0.51* |
| | 26 | 8.92*** | 3.45*** | 77.26**** | 68.93**** | 207.64***** | 314.69***** | 0.28* |

Table 2 Legend
expression: tumor/normal
<1.0x  *
1-2x  **
>2.0x  ***
>10x  ****
>100x  *****

TABLE 3

Enriched Gene Sets from GSEA Analyses Under Various Conditions

| | Comparison | | | |
|---|---|---|---|---|
| | With CIN70 Signature | | Without CIN70 Signature | |
| | Enriched Gene Sets | Leading Edge | Enriched Gene Sets | Leading Edge |
| Normal Adrenal: ACC | | | | |
| Normal | None | CCL2, ADORA2A, CXCL1, | None | CXCL1, CCL2, FPR1, CXCL12, ADORA2A, ADRA2A, S100B |
| ACC | Chromosome organization and biogenesis | TP53, MDM2, RAD51, | Chromatin Binding, JNK Cascade, Chromosome organization and biogenesis, Damaged DNA binding | TP53, TP63, MDM2 |
| Normal Adrenal to low grade ACC | | | | |
| Normal | DNA packaging (driven by HAT1) | CCL2, CXCL1, IL8, S100B, INHA | none | CCL2, CXCL1, IL8, CXCL12, S100B, INHA |
| Low Grade ACC | none | TP53, MDM2, OXA1L, TNIK, FOSB, NSD1, RPS6KA5, SMARCD3, KIF22, NCOA5, RAD51, TTK, BLM, MCM2 | none | TP53, TNIK, RPS6KA5, MDM2 |

TABLE 3-continued

Enriched Gene Sets from GSEA Analyses Under Various Conditions

| | Comparison | | | |
|---|---|---|---|---|
| | With CIN70 Signature | | Without CIN70 Signature | |
| | Enriched Gene Sets | Leading Edge | Enriched Gene Sets | Leading Edge |
| | Normal Adrenal to High Grade ACC | | | |
| Normal | none | CCL2, ADORA2A, FPR1, CXCL12, ADRA2A, CXCL1, CCL11 | none | CCL2, ADORA2A, CXCL1 |
| High Grade ACC | Nuclear Pore, Chromosome organization and biogenesis, Chromatim binding | TP53, MDMD2, NCOA5, RAD51, ILF3 | Thyroid hormone receptor binding, Chromosome organization and biogenesis, Nucleoplasm, RNA splicing, Splicosome complex | TP53, PPARBP, MDM2, CRSP2, THRAP1 |

TABLE 4

Genes showing coordinated expression with CDC2

| Affymetrix | Agilent | Gene Symbol |
|---|---|---|
| NM_014736 | NM_014736 | KIAA0101 |
| NM_014736 | NM_014736 | CSNK1G1 |
| AF213040 | NM_005192 | CDKN3 |
| AF213033 | NM_005192 | CDKN3 |
| NM_002497 | NM_002497 | NEK2 |
| BC028974 | NM_173480 | ZNF57 |
| NM_006101 | NM_006101 | NDC80 |
| NM_018123 | NM_018136 | ASPM |
| NM_016448 | NM_016448 | DTL |
| AK001261 | NM_016448 | DTL |
| AK025578 | NM_013282 | UHRF1 |
| AU153848 | NM_013277 | RACGAP1 |
| NM_022346 | NM_022346 | NCAPG |
| NM_018492 | NM_018492 | PBK |
| NM_018131 | NM_018131 | CEP55 |
| AU159942 | NM_001067 | TOP2A |
| AL561834 | NM_001067 | TOP2A |
| NM_004219 | NM_004219 | PTTG1 |
| AF326731 | NM_145697 | NUF2 |
| NM_004701 | NM_004701 | CCNB2 |
| AF394735 | NM_002358 | MAD2L1 |
| NM_014791 | NM_014791 | MELK |
| NM_007057 | NM_032997 | ZWINT |
| BE407516 | NM_031966 | CCNB1 |
| N90191 | NM_031966 | CCNB1 |
| NM_005196 | NM_016343 | CENPF |
| AF043294 | NM_004336 | BUB1 |
| NM_014750 | NM_014750 | DLG7 |
| AL524035 | NM_001786 | CDC2 |
| NM_001786 | NM_001786 | CDC2 |
| D88357 | NM_001786 | CDC2 |
| NM_001168 | NM_001168 | BIRC5 |
| NM_018685 | NM_018685 | ANLN |
| AK023208 | NM_018685 | ANLN |
| NM_024629 | NM_024629 | MLF1IP |
| AB032931 | NM_014176 | UBE2T |

---

The invention claimed is:

1. A method of prognosing adrenocortical carcinoma in a human patient, the method comprising:
   obtaining a sample of an adrenocortical carcinoma tumor from the human patient;
   determining the level of pTTG1 expression in the tumor sample by:
   a) adding a first oligonucleotide and a second oligonucleotide to a mixture comprising the sample of the adrenocortical carcinoma tumor,
   wherein
      the first and second oligonucleotides are capable of binding to a nucleic acid biomarker comprising SEQ ID NO:1, and
      the first or the second oligonucleotide comprises a sequence selected from the group consisting of: SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, and SEQ ID NO: 21;
   b) subjecting the mixture to conditions that allow detection of the binding of the first and second oligonucleotides to the nucleic acid biomarker; and
   c) calculating the expression of the nucleic acid biomarker through the level of the binding of the first and second oligonucleotides to the biomarker, wherein the expression of the nucleic acid biomarker in the sample is calculated in comparison to the expression of the biomarker in a control sample; and
   classifying the human patient into one of a first cohort of individuals and a second cohort of individuals, individuals of the first cohort and not the second cohort have an at least three-fold increase in expression of SEQ ID NO: 1 in the sample of the adrenocortical carcinoma tumor; and
   prognosing a patient classified in the second cohort as likely to survive for a greater period of time after diagnosis with adrenocortical carcinoma compared to a patient classified in the first cohort.

2. The method of claim 1, wherein the first oligonucleotide and the second oligonucleotide are capable of binding to different nucleic acid strands.

3. The method of claim 2 and further comprising adding a third oligonucleotide to the mixture wherein the third oligonucleotide is capable of binding to a sequence between the sequences to which the first oligonucleotide and the second oligonucleotide are capable of binding.

4. The method of claim 3, wherein the third oligonucleotide comprises a fluorescent label.

5. The method of claim 3, wherein the third oligonucleotide comprises a quencher.

6. The method of claim 2, wherein the nucleic acid amplification is verified by a method selected from the group consisting of a specifically sized band visualized through gel electrophoresis, a Ct value, and DNA sequencing on a product of amplification.

7. The method of claim 1, wherein the human patient is classified into the first cohort of individuals based upon a determination of a three to five fold increase in expression of the biomarker in the sample of the adrenocortical carcinoma tumor.

8. A method of determining a likelihood of survival of a human patient with adrenocortical carcinoma, the method comprising the steps of:
- diagnosing the human patient as having an adrenocortical carcinoma tumor, wherein diagnosing the human patient comprises obtaining a tumor biopsy from the human patient and evaluating the tumor for the presence of adrenocortical carcinoma;
- adding a first oligonucleotide, a second oligonucleotide, and third oligonucleotide to a mixture comprising a sample of the adrenocortical carcinoma tumor in the human patient,
- wherein
  - the first, second, and third oligonucleotides are capable of binding to a nucleotide acid biomarker comprising SEQ ID NO: 1, and
  - the first, second or third oligonucleotide comprises a sequence selected from the group consisting of: SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, and SEQ ID NO: 21;
- subjecting the mixture to conditions that allow detection of the binding of the first, second, and third oligonucleotides to the biomarker; and
- prognosing the human patient as having a decreased likelihood for survival when there is an at least three-fold increase in expression of the biomarker in the sample as compared to a control.

9. The method of claim 8, wherein the human patient is classified as having a decreased likelihood for survival wherein there is a three to five fold increase in expression of the biomarker in the sample compared to the control.

10. The method of claim 8, wherein the third oligonucleotide comprises a fluorescent label.

11. The method of claim 10, wherein the third oligonucleotide comprises a quencher.

12. A method of prognosing and treating adrenocortical carcinoma in a human patient, the method comprising:
- obtaining a sample of an adrenocortical carcinoma tumor from the human patient;
- determining the level of pTTG1 expression in the tumor sample by:
  - a) adding a first oligonucleotide and a second oligonucleotide to a mixture comprising the sample of the adrenocortical carcinoma tumor, wherein the first and second oligonucleotides are capable of binding to a nucleic acid biomarker comprising SEQ ID NO:1;
  - b) subjecting the mixture to conditions that allow detection of the binding of the first and second oligonucleotides to the nucleic acid biomarker; and
  - c) calculating the expression of the nucleic acid biomarker through the level of the binding of the first and second oligonucleotides to the biomarker, wherein the expression of the nucleic acid biomarker in the sample is calculated in comparison to the expression of the biomarker in a control sample; and
- classifying the human patient into one of a first cohort of individuals and a second cohort of individuals, individuals of the first cohort and not the second cohort have an at least three-fold increase in expression of SEQ ID NO: 1 in the sample of the adrenocortical carcinoma tumor;
- prognosing a patient classified in the second cohort as likely to survive for a greater period of time after diagnosis with adrenocortical carcinoma compared to a patient classified in the first cohort; and
- administering an effective amount of an agent that reduces pTTG1 expression to the patient classified into the first cohort.

13. The method of claim 12, wherein the agent is Vorinostat.

14. The method of claim 12, wherein the first oligonucleotide and the second oligonucleotide are capable of binding to different nucleic acid strands.

15. The method of claim 14, further comprising adding a third oligonucleotide to the mixture wherein the third oligonucleotide is capable of binding to a sequence between the sequences to which the first oligonucleotide and the second oligonucleotide are capable of binding.

16. The method of claim 15, wherein the third oligonucleotide comprises a fluorescent label.

17. The method of claim 15, wherein the third oligonucleotide comprises a quencher.

18. The method of claim 14, wherein the nucleic acid amplification is verified by a method selected from the group consisting of a specifically sized band visualized through gel electrophoresis, a Ct value, and DNA sequencing on a product of amplification.

19. The method of claim 12, further comprising first diagnosing the human patient as having an adrenocortical carcinoma tumor, wherein diagnosing the human patient comprises obtaining a tumor biopsy from the patient and evaluating the tumor for the presence of adrenocortical carcinoma.

20. The method of claim 12, wherein the human patient is classified into the first cohort of individuals based upon a determination of a three to five fold increase in expression of the biomarker in the sample of the adrenocortical carcinoma tumor.

* * * * *